United States Patent [19]
Weis et al.

[11] Patent Number: 5,939,402
[45] Date of Patent: Aug. 17, 1999

[54] NUCLEOSIDE ANALOGS AND USES AGAINST PARASITIC INFECTION

[75] Inventors: Alexander L. Weis; Kirupathevy Pulenthiran, both of San Antonio, Tex.

[73] Assignee: Lipitek International, Inc., San Antonio, Tex.

[21] Appl. No.: 09/038,647

[22] Filed: Mar. 11, 1998

Related U.S. Application Data

[63] Continuation-in-part of application No. 08/531,875, Sep. 21, 1995.

[51] Int. Cl.$^6$ .................................................. A61K 31/70
[52] U.S. Cl. ................................. 514/44; 514/45; 514/46; 514/47; 514/48; 514/49; 514/50; 514/51; 514/895
[58] Field of Search .................................. 514/45, 46, 47, 514/48, 49, 50, 51, 42, 44, 43, 895

[56] References Cited

U.S. PATENT DOCUMENTS

| 5,552,535 | 9/1996 | McLean et al. . |
| 5,571,902 | 11/1996 | Ravikomar et al. . |
| 5,608,046 | 3/1997 | Cook et al. . |
| 5,614,505 | 3/1997 | Gmeiner et al. . |

*Primary Examiner*—James O. Wilson
*Attorney, Agent, or Firm*—Fulbright & Jaworski L.L.P.

[57] ABSTRACT

The invention relates to novel nucleosides and nucleoside dimers containing an L-sugar in at least one of the nucleosides, and their pharmaceutical compositions.

6 Claims, 14 Drawing Sheets

A.)

B.)

| f | R₁=α-L-5-fluorouracil, R₂=β-D-5-fluorouracil |
|---|---|
|   | X= Me, CH₂CH₂CN |

Methoxy phosphotriesters

Methyl phosphonates

Phosphorodithioates

Silyl Ethers

Sulfonates

Ethylenedioxy ethers

Phosphorothioates

NUCLEOSIDE ANALOGS AND USES AGAINST PARASITIC INFECTION

This application is a continuation-in-part from U.S. patent application Ser. No. 08/531,875, filed on Sep. 21, 1995.

BACKGROUND OF THE INVENTION

1. Field of Invention

This invention relates to novel nucleosides and dinucleoside dimers and derivatives of these compounds, including, L-deoxyribofuranosyl nucleoside phosphodiester dimers in which the sugar moiety of at least one of the nucleosides has an L-configuration. These compounds are highly effective in the treatment of various diseases, in particular the infection of the protozoan parasite, *Plasmodium falciparum*, the etiologic agent responsible for the most fatal form of malaria.

2. Prior Art

Modified nucleoside analogs are an important class of antineoplastic and antiviral drugs. The present application discloses novel compounds for of this type for use in the treatment of *P. falciparum* infection. *Plasmodium falciparum* is the etiologic agent responsible for the most fatal form of malaria, a disease which afflicts between 200 and 300 million people per year (all forms), including over one million childhood deaths. Additionally, greater than 40% of the world's population lives in areas in which malaria is at epidemic levels. Due to the extraordinary morbidity and mortality associated with malaria, malaria-related research has intensified during the past decade in a desperate search for an effective treatment. A safe and effective vaccine still does not exist. Instead, malaria victims must depend upon chemotherapy.

These chemotherapeutic agents can be classified into two groups: those that act post-translationally, and those that act by interfering with nucleic acid synthesis.

Most antimalarial drugs are in the first group, which means that they exert their therapeutic effect by interfering with the parasite cell's protein synthesis, and hence its metabolism (rather than its nucleic acid synthesis). Examples of drugs in this group include: the antifolate compounds (which inhibit dihyrdofolate reductase), and sulfonamide drugs (which inhibit dihydropteroate synthetase. Yet these drugs have serious drawbacks. Perhaps the most serious is that the protozoan responsible for malaria very quickly develops resistance to these drugs. The reason is that, since resistance occurs through adaptive mutations in successive generations of the parasite, one or two point mutation is often sufficient to confer resistance.

The second group of antimalarial compounds includes the nucleic acid intercalators such as acridines, phenanthrenes and quinolines. These intercalators partially mimic the biochemical activity of nucleic acids, and therefore are incorporated into the cell's nucleic acid (DNA and RNA), though once incorporated, do not allow further nucleic acid synthesis, hence their effectiveness. At the same time, these intercalators interfere with host nucleic acid synthesis as well, and thus give rise to toxic side effects. Because of the potential for toxic side effects, these drugs can quite often be given only in very small doses. Moreover, the protozoan responsible for malaria is known to develop "cross-resistance," which means that the parasite develops resistance to other classes of drugs even though it was exposed on a different class of drug.

Indeed, all of the currently known antimalarial drugs or drug candidates utilizing the delivery of cytotoxic pyrimidine or purine biosynthesis inhibitor to the malarial parasite are extremely toxic. Therefore, while drugs of this type—i.e., those that interfere with malarial parasite's nucleic acid synthesis-are effective, they lack selectivity. It is this latter parameter that must be maximized in the development of a safe and effective antimalarial drug. In other words, such a drug would target host tissues that are infected with the malarial protozoan yet leave the host tissue unchanged.

Recent advances in our understanding of the unusual biochemistry of parasite cells may prove valuable toward the design of an effective antimalarial therapy. One investigator (H. Ginsburg, Biochem. Pharmacol. 48, 1847–1856 (1994)) has observed that normal and parasite-infected erythrocytes exhibit significant differences with respect to purine and pyrimidine metabolism in single enzymes, as well as in whole branches of related pathways. The parasite satisfies all of its purine requirements through scavenger pathways; meanwhile, the host cell lacks the enzymes necessary to exploit this pathway, and so therefore must meet its pyrimidine requirements largely through de novo synthesis. Put another way, the parasite is more efficient than normal or host cells since it can synthesize the nucleic acid building blocks.

Other investigators (G. Beaton, D. Pellinqer, W. S. Marshall & M. H. Caruthers, In: *Oligonucleotides and Analogues: A Practical Approach*, F. Eckstein Ed., IRL Press, Oxford, 109–136 (1991)) have established that a malaria-infected erythrocyte is capable of effectively transporting the non-naturally occurring "L-nucleosides" (in contrast to the "D-nucleosides" which are the naturally occurring form) for use in nucleic acid synthesis. Yet, normal mammalian cells are nonpermeable to this class of compounds, which suggests that the L-nucleosides are non-toxic to normal mammalian or host cells. Thus, derivatives of these compounds may be used as highly selective drugs against parasite infection. The chemical modification of the L-nucleosides consists generally of modifying the nucleosides so that they are still recognized by the parasite's nucleic acid synthetic machinery, and therefore incorporated into a nucleic acid chain, but yet once this incorporation occurs, no further synthesis will take place.

Currently, there are no therapeutic compounds in use that are based on dimers of these nucleoside analogs. While dimers of the naturally occurring D-deoxyribofuranosyl nucleosides are well known, dimers in which one or both nucleosides are of the unnatural L-configuration are much less known, and their use in therapy of neoplastic and viral diseases is unknown.

In the synthesis of DNA-related oligomers, types of nucleoside dimers are synthesized as part of the overall process. These dimers usually include bases from naturally occurring DNA or RNA sequences. There is much known in the art about nucleoside monophosphate dimers. Many of these compounds have been synthesized and are available commercially. However, these dimers are made from nucleosides containing a sugar moiety in D-configuration.

Reese, C. B., Tetrahedron 34 (1978) 3143 describes the synthesis of fully-protected dinucleoside monophosphates by means of the phosphotriester approach.

Littauer, U. Z., and Soreg, H. (1982) in *The Enzymes*, Vol. XV, Academic Press, NY, p. 517 is a standard reference which describes the enzymatic synthesis of dinucleotides.

Heikkilö, J., Stridh, S., Öberg, B. and Chattopodhyaya, J., Acta Chem. Scand. B 39 (1985) 657–669, provides an example of the methodology used in the synthesis of a variety of ApG nucleoside phosphate dimers. Included are references and methods for synthesis of 3'→5' phosphates and 2'→5' phosphates by solution phase chemistry.

Gait, M., "Oligonucleotide Synthesis", IRL Press, Ltd., Oxford, England, 1984, is a general reference and a useful overview for oligonucleotide synthesis. The methods are applicable to synthesis of dimers, both by solution phase and solid phase methods. Both phosphitetriester and phosphotriester methods of coupling nucleosides are described. The solid phase method is useful for synthesizing dimers.

Gulyawa, V. and Holy, A., Coll. Czec. Chem. Commun 44 613 (1979), describe the enzymatic synthesis of a series of dimers by reaction of 2',–3' cyclic phosphate donors with ribonucleoside acceptors. The reaction was catalyzed by non-specific RNases. The donors are phosphorylated in the 5'-position, yielding the following compounds: donor nucleoside-(3'→5') acceptor nucleoside. Dimers were made with acceptors, β-L-cytidine, β-L-adenosine, and 9(α-L-lyxofuranosyl) adenine. Also, a large number of dimers with D-nucleosides in the acceptor 5'-position were made.

Holy, A., Sorm, F., Collect. Czech. Chem. Commun., 34, 3383 (1969), describe an enzymatic synthesis of β-D-guanylyl-(3'→5')-β-L-adenosine and β-D-guanylyl-(3'→5')-β-L-cytidine.

Schirmeister, H. and Pfleiderer, W., Helv. Chim. Acta 77, 10 (1994), describe trimer synthesis and intermediate dimers, all from β-D-nucleosides. They used the phosphoramidite method which gave good yields.

Thus, dimers with L-deoxyribofuranosyl moieties in any position are new, as are dimers with L-ribofuranosyl moieties bonded to the 3'-position of the phosphate internucleotide bond.

Modified nucleoside analogues represent an important class of compounds in the available arsenal 3'of antineoplastic and antiviral drugs. The anticancer agents 5-fluorodeoxyuridine (floxuridine), cytarabine and deoxycoformycin and the antiviral drugs 3'azidodeoxythymidine (AZT), dideoxycytidine (ddC), dideoxyinosine (ddI), acyclovir, 5-iododeoxyuridine (idoxuridine) fludarabine phosphate and vidarabine (adenine arabinoside/ara A) are representative of this class of monomeric nucleoside-derived compounds which are used therapeutically.

More recently, "antisense" oligonucleotide analogues with modified bases and/or phosphodiester backbones have been actively pursued as antiviral and antitumor agents. While no clinically approved drug has yet emerged from this class of compounds, it remains a very active field of research. Recently, antipodal L-sugar-based nucleosides also have found application as potent antiviral agents because they can inhibit viral enzymes without affecting mammalian enzymes, resulting in agents that have selective antiviral activity without concomitant mammalian cytotoxicity.

Most naturally occurring nucleosides have the D-configuration in the sugar moiety. While the chemical properties of L-nucleosides are similar to those of their β-D-enantiomers, they exhibit very different biological profiles in mammalian cells and do not interfere with the transport of normal D-nucleosides. For example, β-L-uridine is not phosphorylated at the 5'-position by human prostate phosphotransferase, which readily phosphorylates the enantiomeric β-D-uridine. Apparently, L-nucleosides are not substrates for normal human cell kinases, but they may be phosphorylated by viral and cancer cell enzymes, allowing their use for the design of selective antiviral and anti-cancer drugs.

Oligonucleotides based on L-nucleosides have been studied previously. Octamers derived from α- and β-L-thymidine were found resistant to fungal nucleases and calf spleen phosphodiesterase, which readily degrades the corresponding β-D-oligonucleotide. Fujimory, et al., S. Fujimory, K. Shudo, Y. Hashimoto, J. Am. Chem. Soc., 112, 7436, have shown that enantiomeric poly-α-DNA recognizes complementary RNA but not complementary DNA. This principle has been used in the design of nuclease-resistant antisense oligonucleotides for potential therapeutic applications.

Thus, L-nucleoside-based compounds have potential as drugs against neoplastic and viral diseases. While L-sugar-derived nucleosides and their oligonucleotides have been widely evaluated for such activities, little is known regarding the biological activities of shorter oligomers such as dimers obtained by L-nucleoside substitution.

This invention comprises novel L-nucleoside-derived therapeutic antitumor and antiviral agents. Novel L-nucleoside-derived dinucleoside monophosphates, based on L-α-5-fluoro-2'-deoxyuridine showed a remarkably high potency activity profile in in vitro anti-cancer assays, with indications of unique mechanisms of action, including inhibition of telomerase. Therefore, the L-nucleosides can serve as building blocks for new drugs with the special advantage of low toxicity.

SUMMARY OF THE INVENTION

A further embodiment of the present invention is the administration of a therapeutically effective amount of the compounds of the present invention for the treatment of cancer or viral infections.

Other and further objects, features and advantages will be apparent from the following description of the present preferred embodiments of the invention given for the purposes of disclosure when taken in conjunction with the accompanying drawings.

Certain features of the invention may be exaggerated in scale or shown in schematic form in accordance with the customary practices in the biochemical arts.

DETAILED DESCRIPTION OF THE PREFERRED EMBODIMENTS

It is readily apparent to one skilled in the art that various substitutions and modifications may be made to the invention disclosed in this Application without departing from the scope and spirit of the invention.

Figure 1:
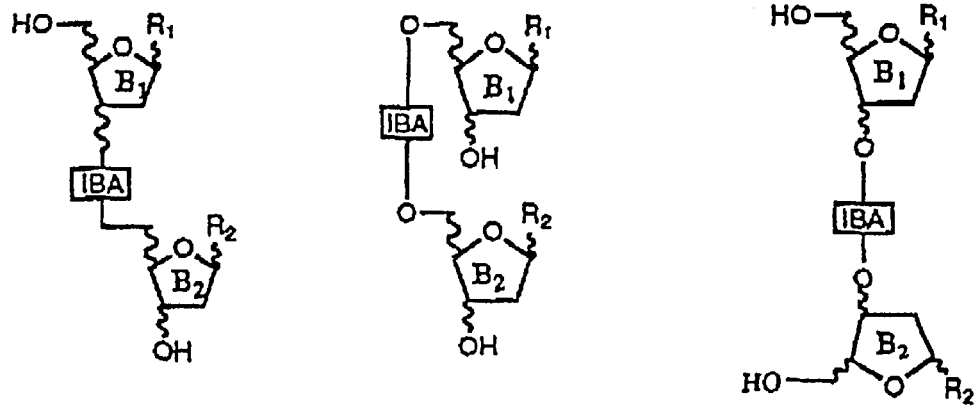
FIG. 1 is a schematic representation of the dinucleotide dimers of the present invention.
Figure 1:
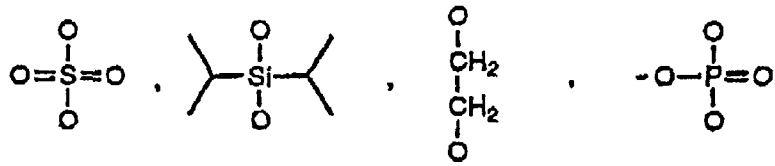
Figure 2:
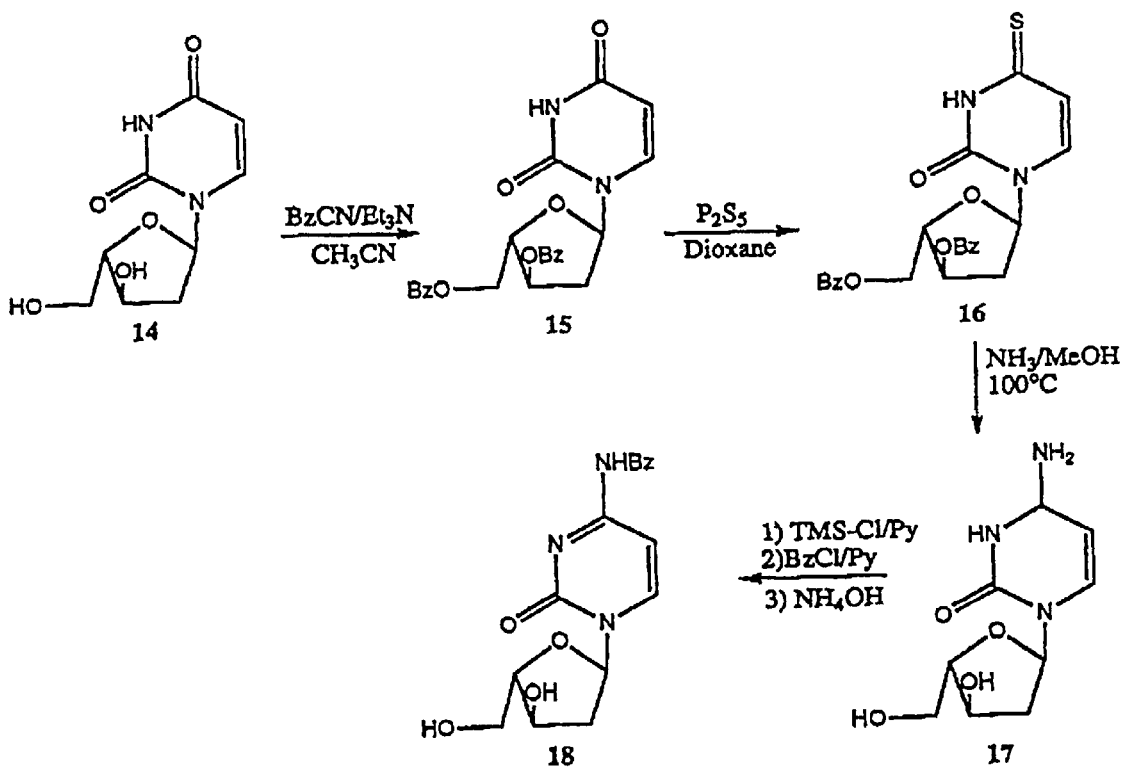
FIGS. 2A, 2B and 3–5 are schematic representations of the synthesis scheme followed in the present invention.
Figure 2A:
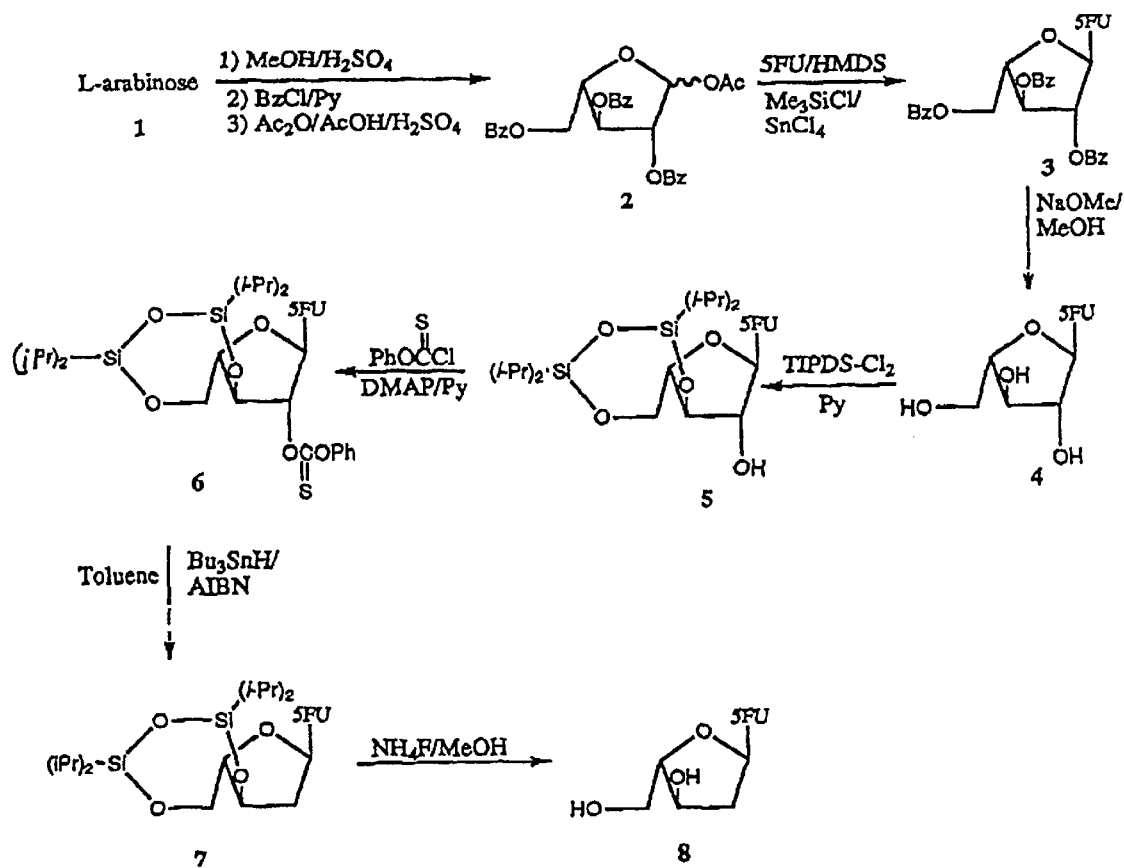
Figure 2B:
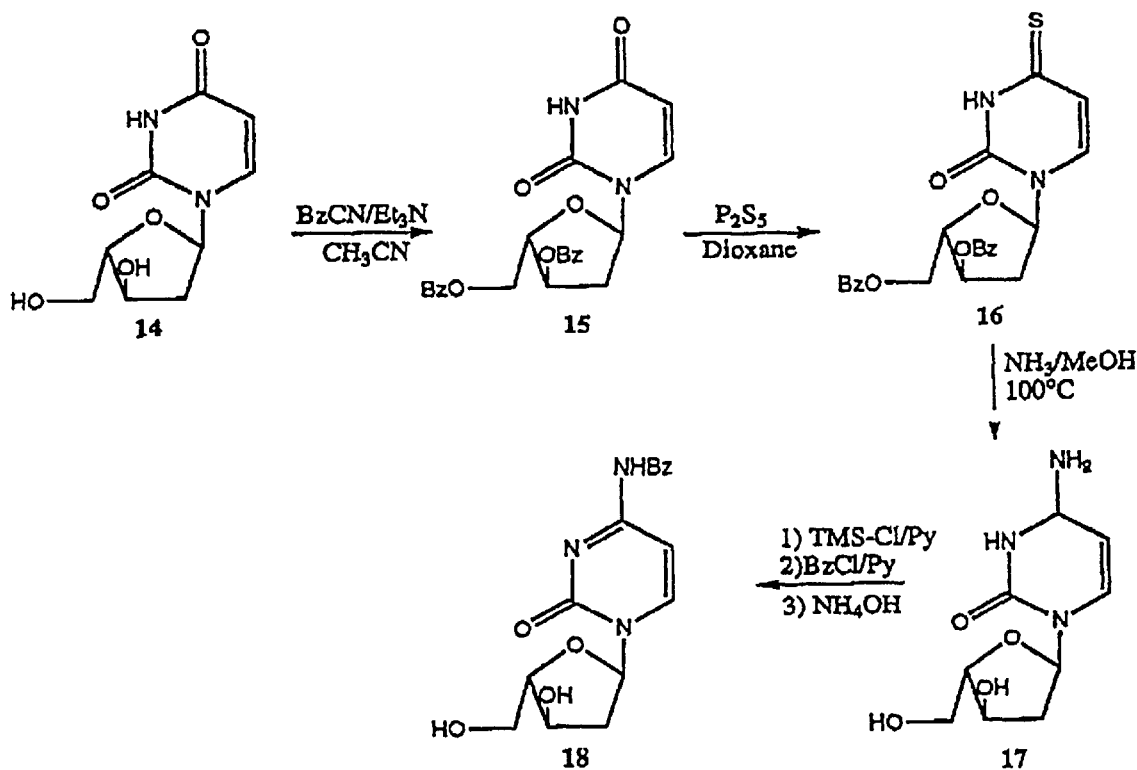
Figure 3:
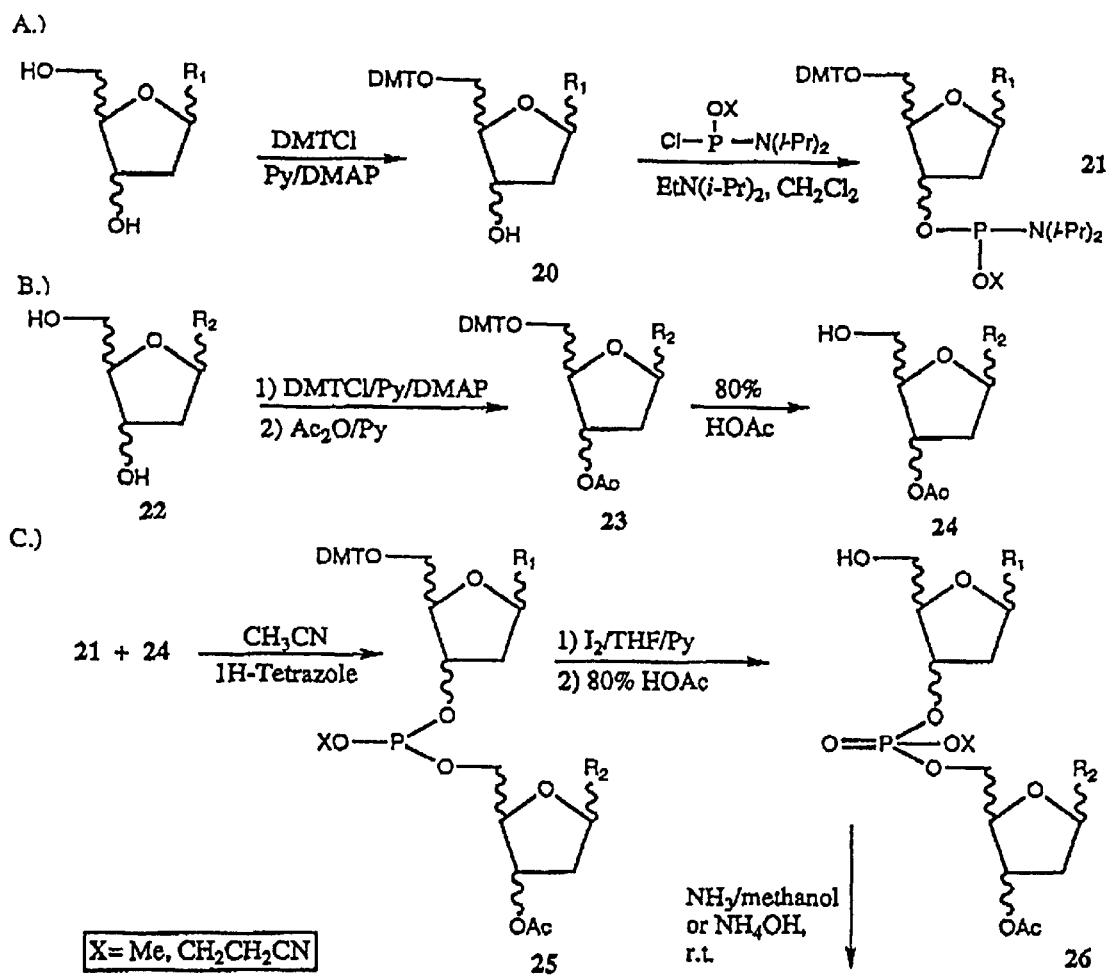
Figure 3:
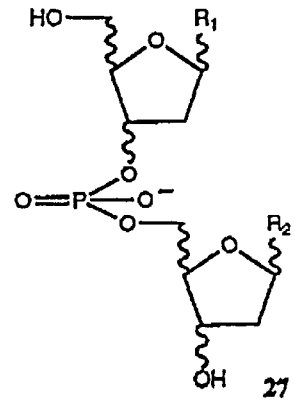
Figure 4:
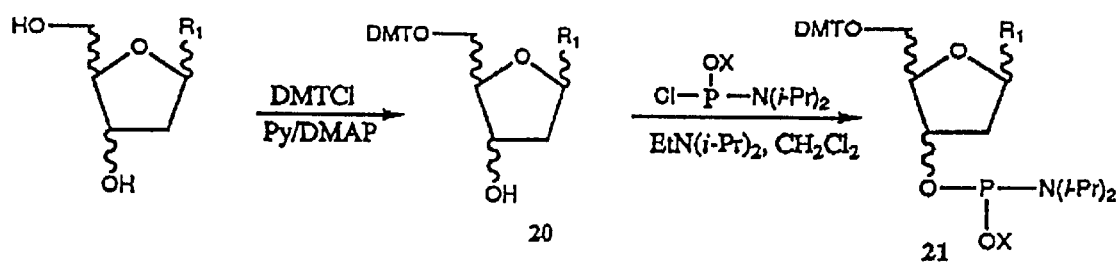
Figure 4:
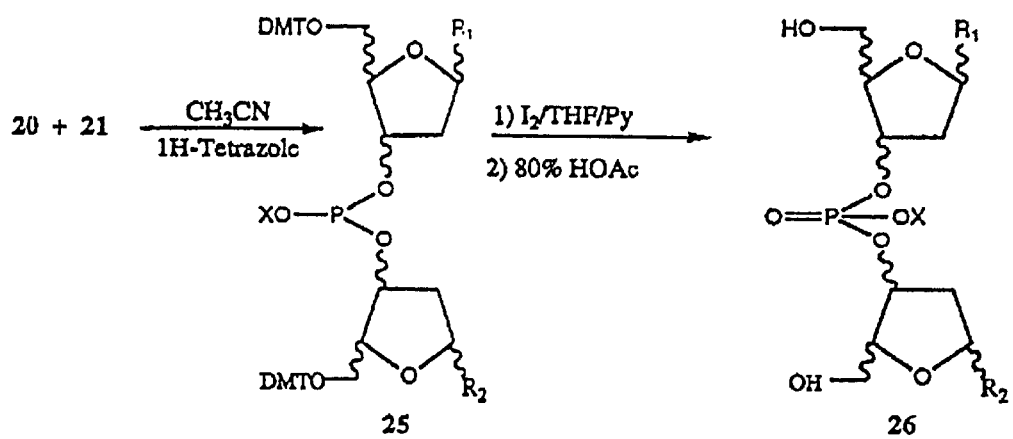
Figure 4:
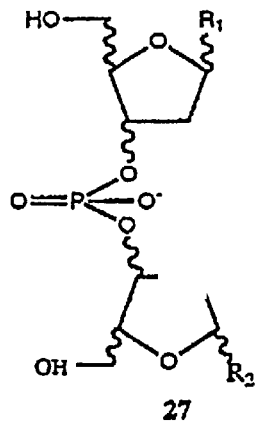
Figure 5:
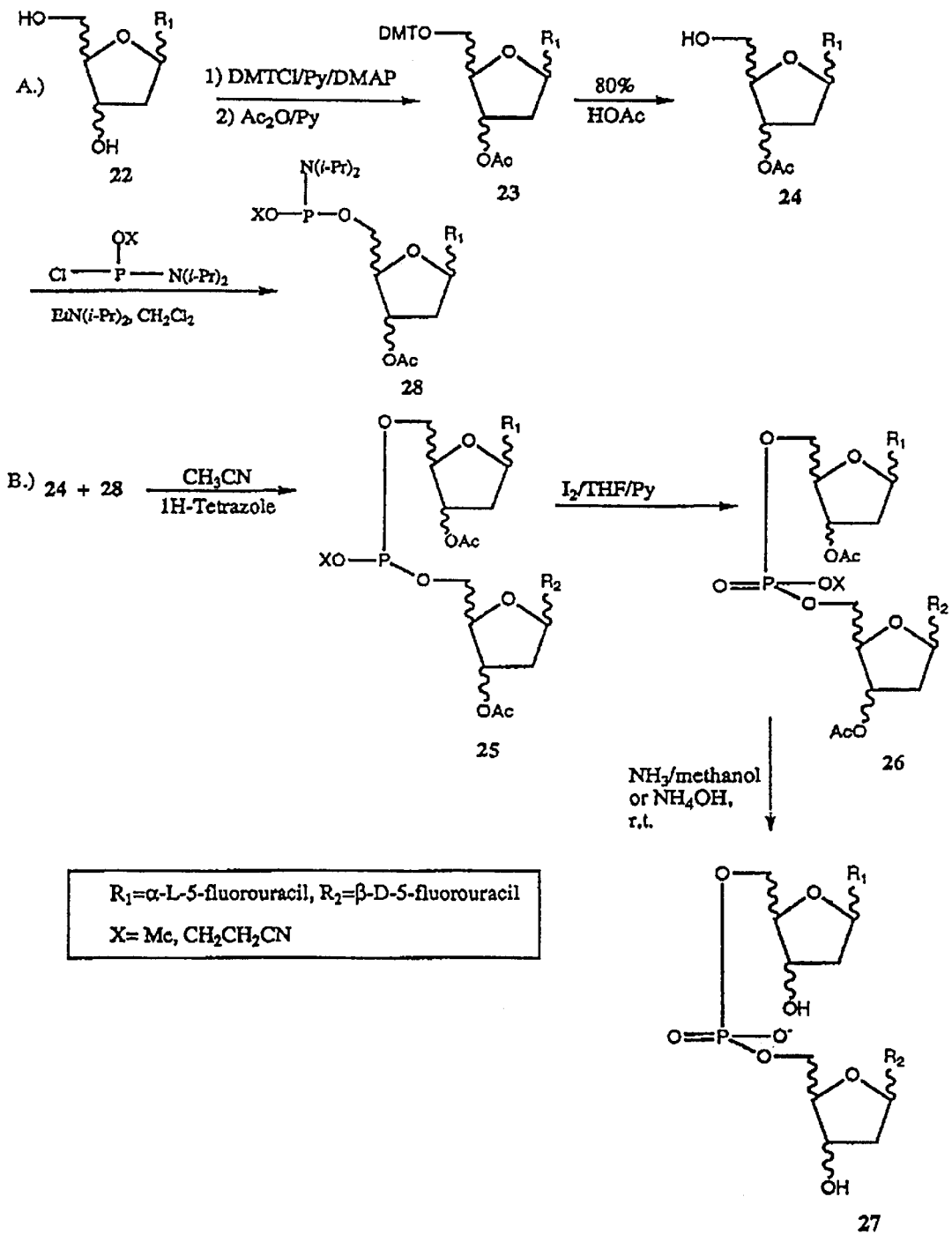
Figure 6A:
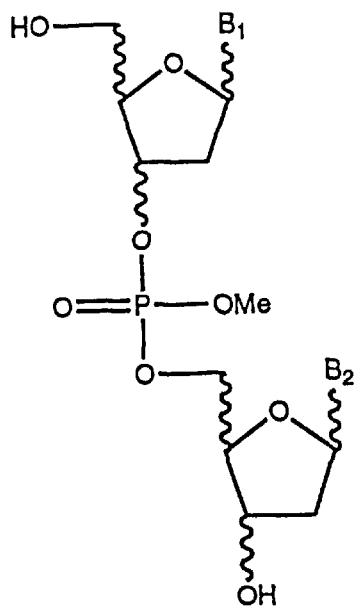
FIGS. 6A and 6B are schematic representations of dinucleoside phosphate dimers containing alternate backbones.
Figure 6A:
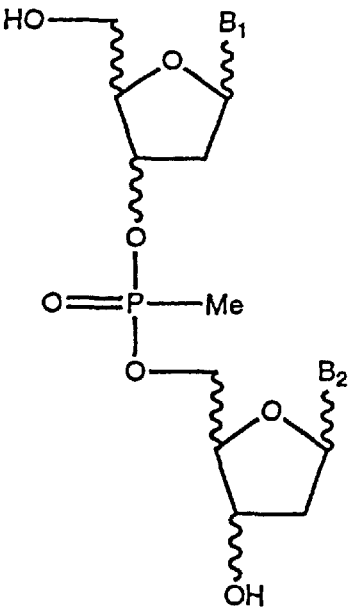
Figure 6A:
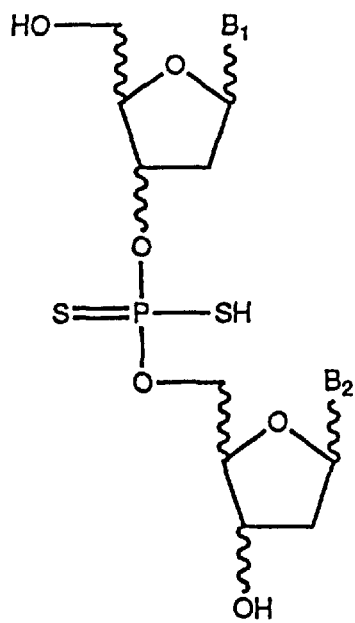
Figure 6A:
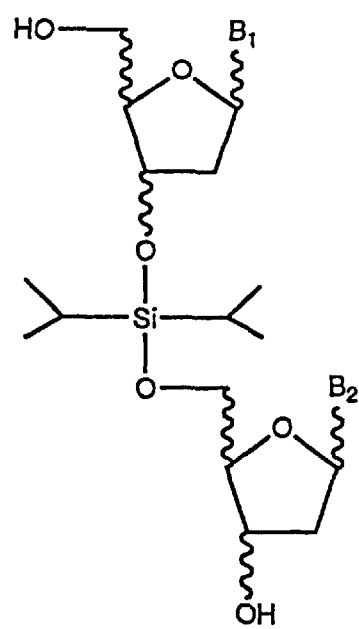
Figure 6B:
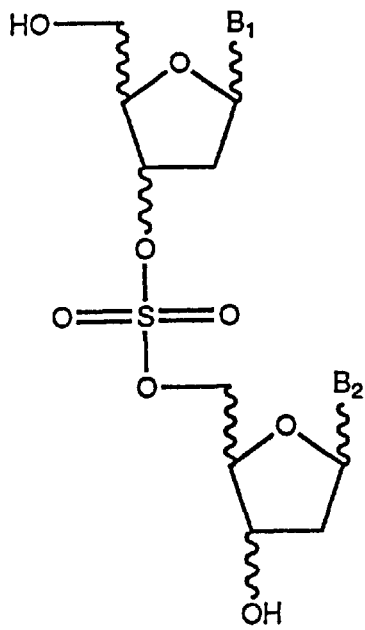
Figure 6B:
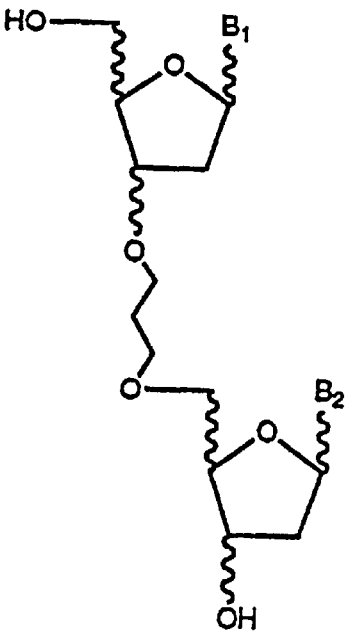
Figure 6B:
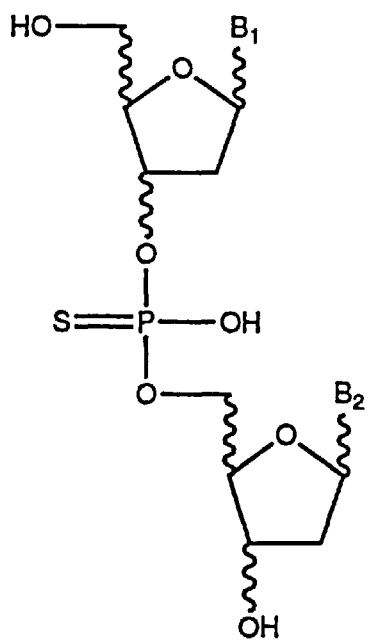
Figure 7A:
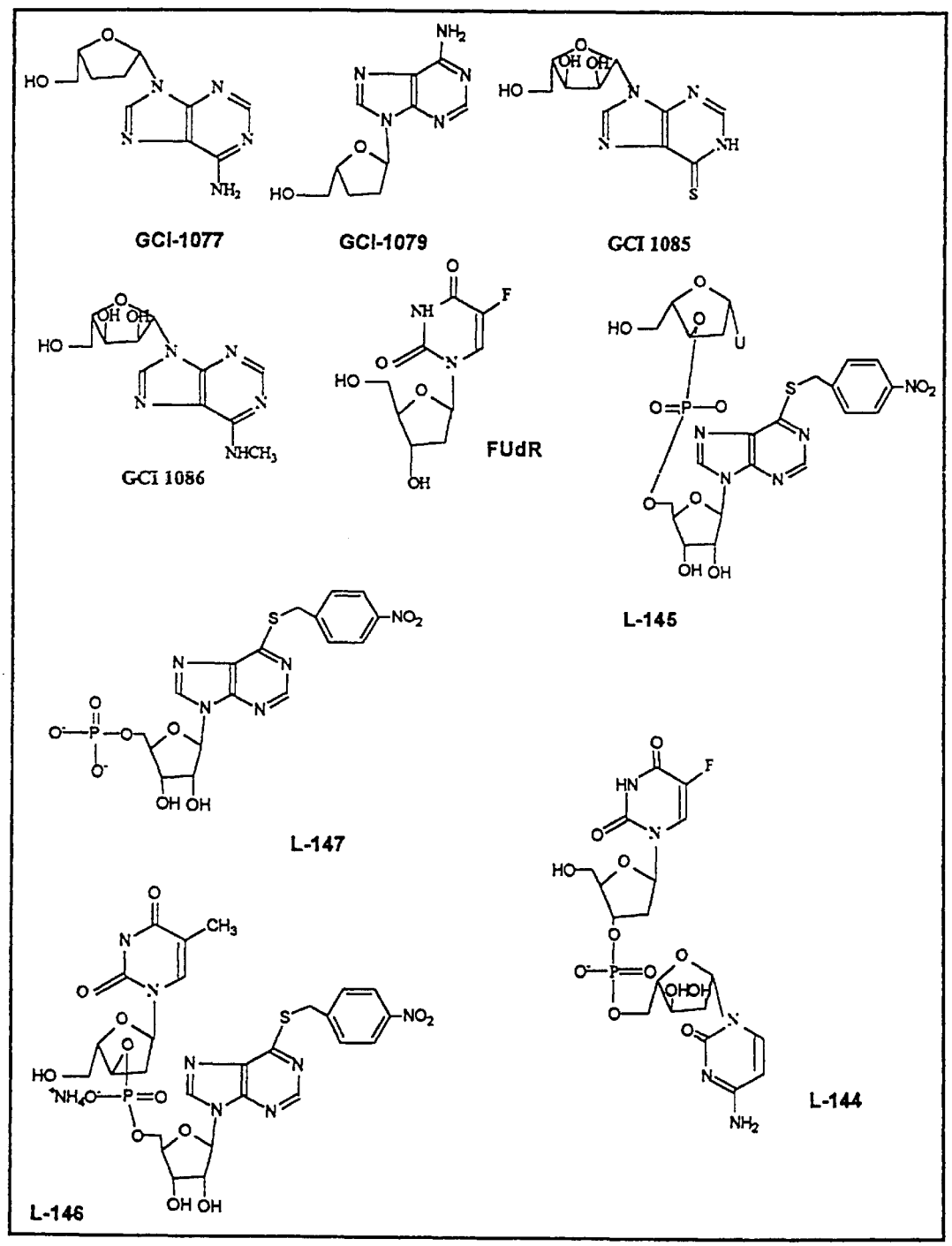
FIG. 7 is schematic representations of dinucleoside phosphate dimers used in the examples.
Figure 7B:
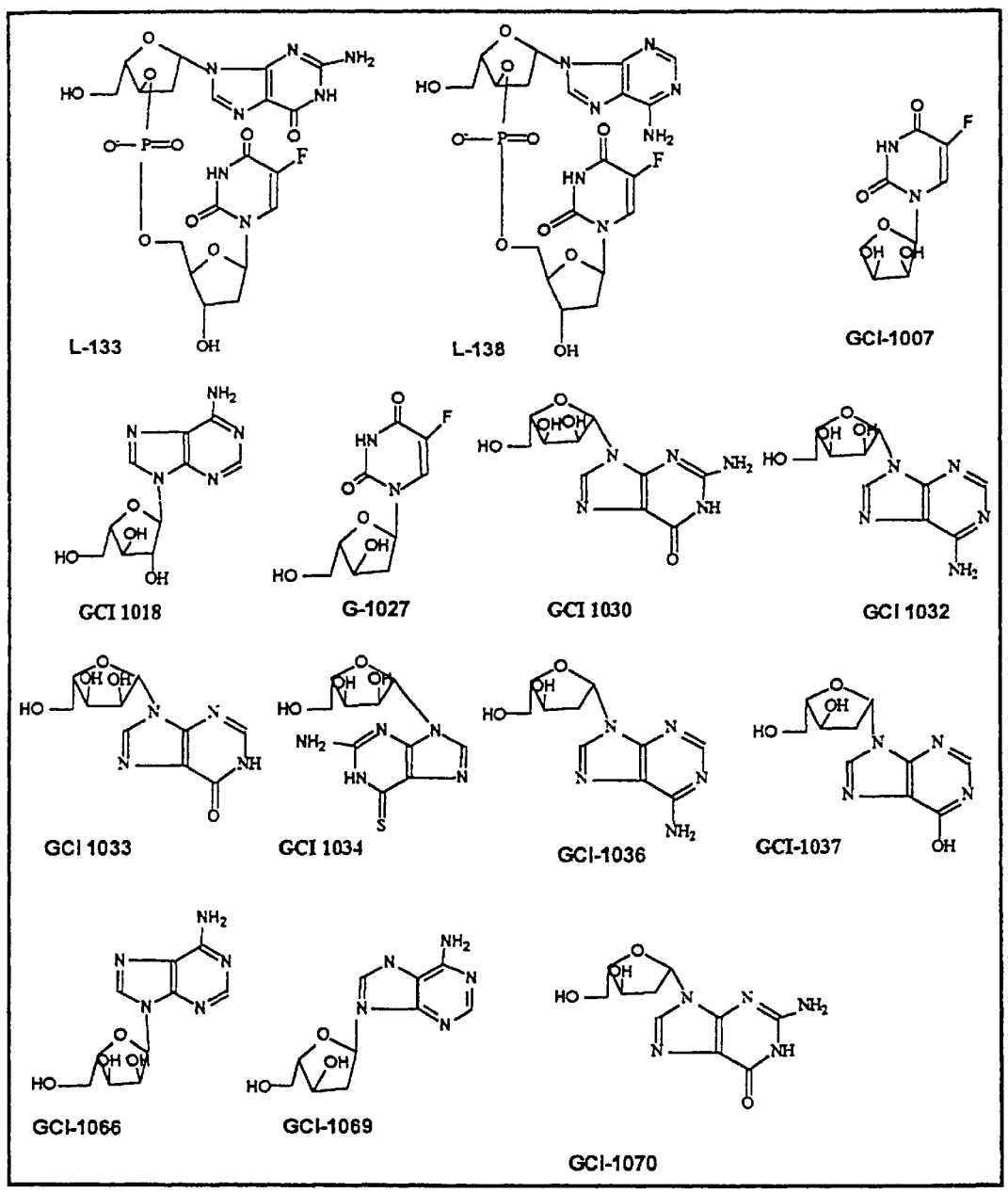
Figure 7C:
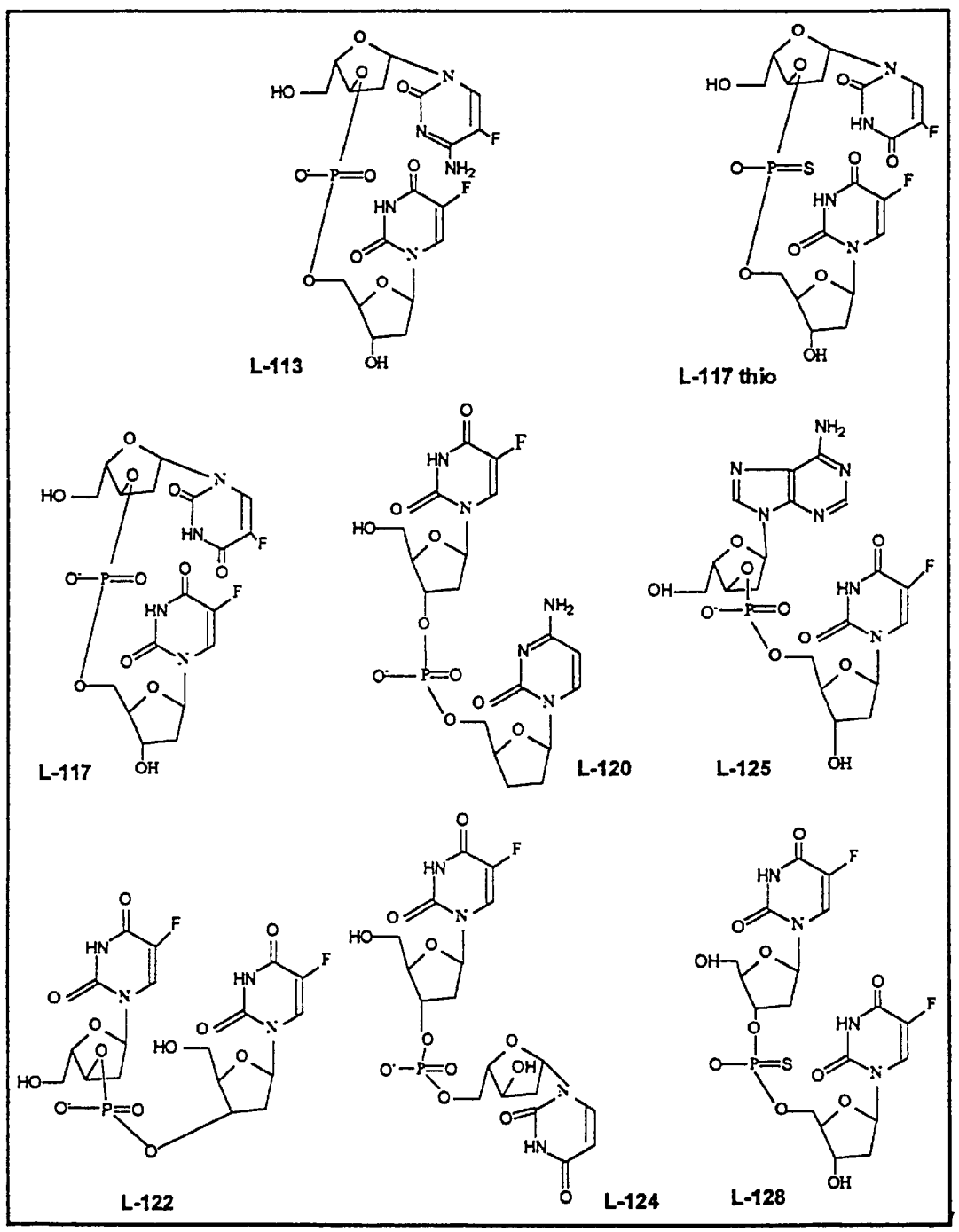
Figure 7D:
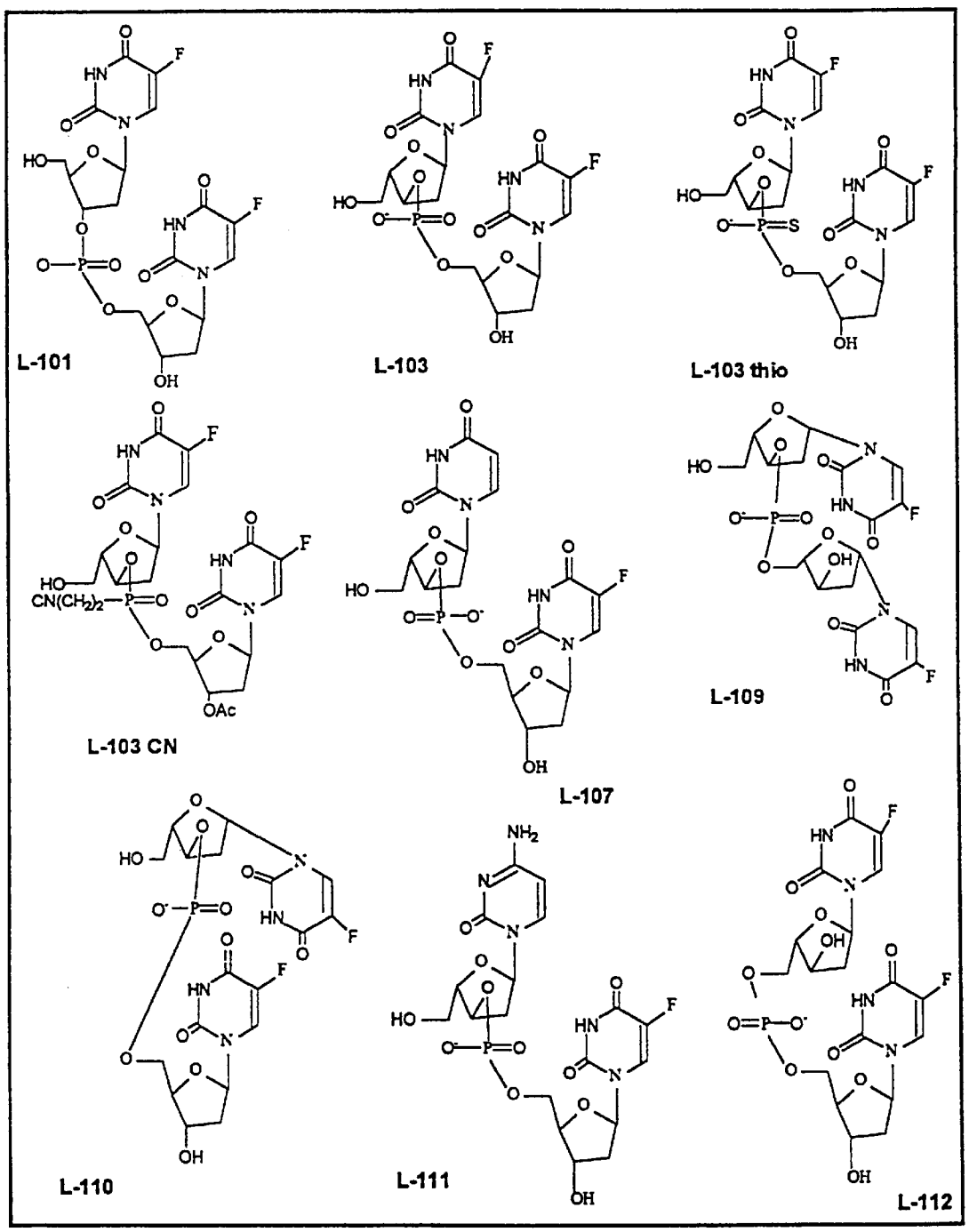
Figure 7E:
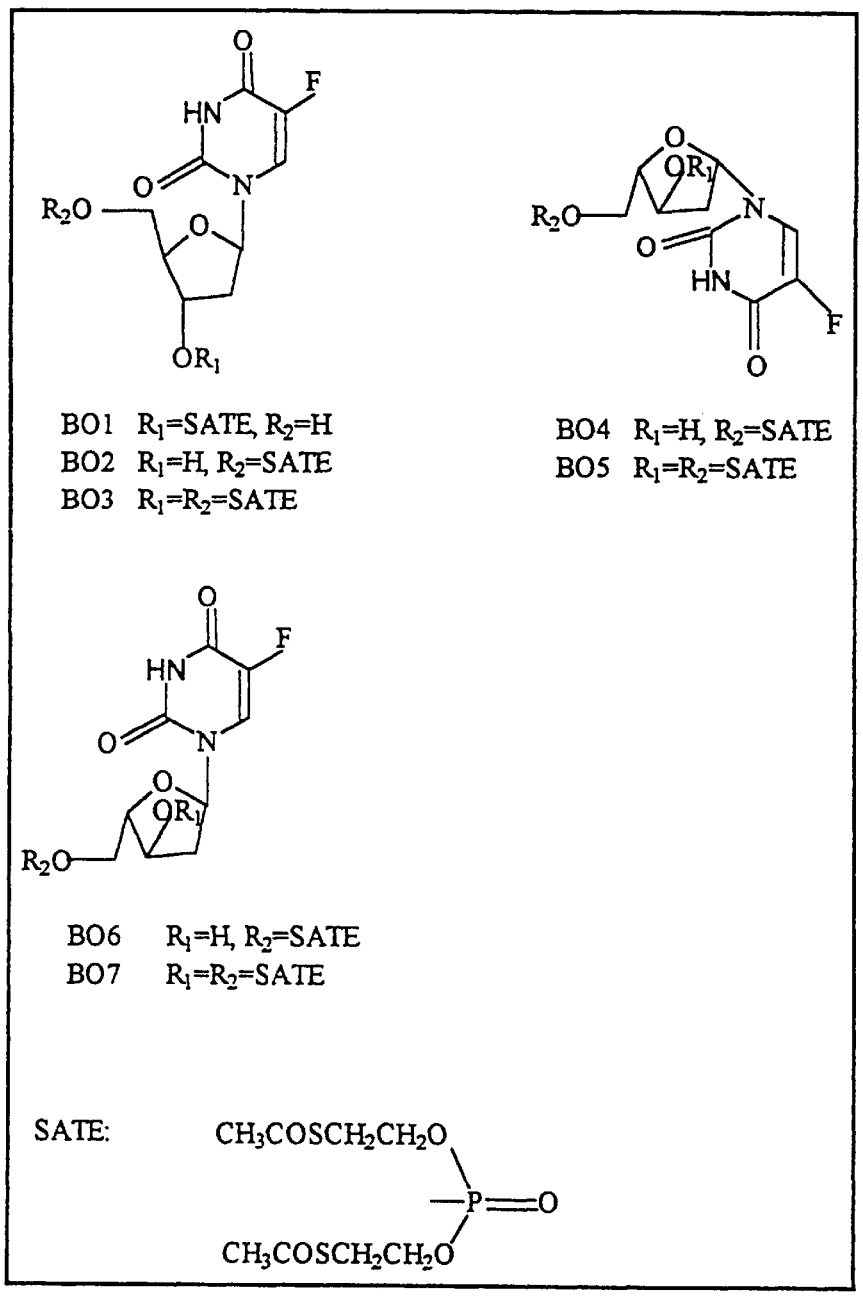

The term "dimers" as used herein is defined by the structures shown in FIG. 1. These compounds are L-nucleoside-derived dinucleoside monophosphates. The $B_1$ and $B_2$ units will consist of either a β-D, a β-L or an α-L nucleoside and at least one of $B_1$ or $B_2$ will be β-L or α-L. $R_1$ and $R_2$ will be the pyrimidine bases cytosine, thymine, uracil, or 5-fluorouridine (5-FUdR) other 5-halo compounds, or the purine bases, adenosine, guanosine or inosine. As can be seen in FIG. 1, the dimers can be bound either 5'→3', 3'→5', 3'→3', or 5'→5'.

Specific antidisease compounds which are useful in the present invention include 3'-O-(α-L-5-fluoro-2'-deoxyuridinyl)-β-D-5-fluoro-2'-deoxyuridine, (L-102), 3'-O-(β-D-5-fluoro-2'-deoxyuridinyl)-α-L-5-fluoro-2'-deoxyuridine, (L-103), 3'-O-(β-L-5-fluoro-2'-deoxyuridinyl)-α-L-2'-deoxyuridine, (L-107), 3'-O-(α-L-5-fluoro-2'-deoxyuridinyl)-α-L-5-fluoro-2'-deoxyuridine, (L-108), 3'-O-(β-L-5-fluoro-2'-deoxyuridinyl)-β-L-5-fluoro-2'-deoxyuridine, (L-109), 3'-O-(β-D-5-fluoro-2'-deoxyuridinyl)-β-L-5-fluoro-2'-deoxyuridine, (L-110), 3'-O-(P-D-5-fluoro-2'-deoxyuridinyl)-α-L-2'-deoxycytidine, (L-111), 3'-O-(β-D-5-fluoro-2'-deoxyuridinyl)-2'-deoxy-β-L-cytidine (L-113), 3'-O-(2'-deoxy-β-L-cytidinyl)-β-D-5-fluoro-2'-deoxyuridine (L-114), 3'-O-(2'-deoxy-α-L-cytidinyl)-β-D-5-fluoro-2'-deoxyuridine (L-115), 3'-O-(β-D-5-fluoro-2'-deoxyuridinyl)-β-L-2'-deoxyuridine (L-117), 3'-O-(β-L-5-fluoro-2'-deoxyuridinyl)-α-L-5-fluoro-2'-deoxyuridine (L-119), 3'-O-(β-D-5-fluoro-2'-deoxyuridinyl)-α-L-5-fluoro-2'-deoxyuridine (3', 3') (L-122). In the currently preferred embodiment, 3'-O-(β-D-5-fluoro-2'-deoxyuridinyl)-α-L-5-fluoro-2'-deoxyuridine, (L-103) is used.

The term "internucleotide binding agent" or "IBA" means the backbone binding which links the nucleosides together. Although one skilled in the art will readily recognize a variety of other backbones are available and useful in the present invention. For example, see FIG. 6, where methoxy phosphotriesters, methylphosphonates, phosphorodithioates, phosphorothioates, silyl ethers, sulphonates and ethylenedioxy ethers are shown. Although shown schematically 3'–5' the IBA's can be used to link the sugars 5'→3', 3'→5', 3'→3', or 5'→5'. In the preferred embodiment, the IBA of the compounds is either phosphodiester or phosphorothioate.

The term "antidisease" as used herein refers to any of the activities of the compounds of the present invention to affect a disease state, including antitumor, antineoplastic, anticancer, antiparasitic and antiviral activity.

A compound or composition is said to be "pharmacologically acceptable" if its administration can be tolerated by a recipient mammal. Such an agent is said to be administered in a "therapeutically effective amount" if the amount administered is physiologically significant. An agent is physiologically significant if its presence results in technical change in the physiology of a recipient mammal. For example, in the treatment of cancer or neoplastic disease, a compound which inhibits the tumor growth or decreases the size of the tumor would be therapeutically effective; whereas in the treatment of a viral disease, an agent which slows the progression of the disease or completely treats the disease, would be considered therapeutically effective.

Dosage and Formulation

The antidisease compounds (active ingredients) of this invention can be formulated and administered to inhibit a variety of disease states (including tumors, neoplasty, cancer, parasitic and viral diseases) by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosages given as examples herein are the dosages usually used in treating tumors, neoplasty and cancer. Dosages for antiparasitic and antiviral applications will, in general, be 10–50% of the dosages for anticancer applications.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. Usually a daily dosage (therapeutic effective amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 to about 500 milligrams of active ingredient per unit. In these pharmaceutical compositions, the active ingredient will ordinarily be present in an amount of about 0.05–95% by weight based on the total weight of the composition.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium EDTA. In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyaminoacids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyaminoacids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows.

Capsules

Capsules are prepared by filling standard two-piece hard gelatin capsulates each with 100 milligram of powdered active ingredient, 175 milligrams of lactose, 24 milligrams of talc and 6 milligrams magnesium stearate.

Soft Gelatin Capsules

A mixture of active ingredient in soybean oil is prepared and injected by means of a positive displacement pump into gelatin to form soft gelatin capsules containing 100 milligrams of the active ingredient. The capsules are then washed and dried.

Tablets

Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable

A parenteral composition suitable for administration by injection is prepared by stirring 1.5% by weight of active ingredients in 10% by volume propylene glycol and water. The solution is made isotonic with sodium chloride and sterilized.

Suspension

An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Summary of Compounds Synthesized

The following examples are offered by way of illustration and are not intended to limit the invention in any manner. The synthetic nucleosides and dimers described in the examples can include any of the substitutions discussed earlier. The backbone and base modifying groups can be added. The substitutions will enhance its affinity, the chemical stability and the cellular uptake properties of the specific dimers treatments.

EXAMPLE 1

Synthesis of 2'-deoxy-α-L-5-flourouridine

While β-D-5-fluoro-deoxyuridine is commercially available, the α-L-isomer 2'-deoxy-α-L-5-fluorouridine is not, and this component of the dimers was synthesized from L-arabinose.

1-(2', 3', 5'-tri-O-benzoyl-α-L-arabinofuranosyl)-5-fluorouracil (3)

To a mixture of 5-fluorouracil (4.01 g, 30.87 mmol) and compound 2 (15.57 g, 30.87 mmol) in anhydrous MeCN were successively added HMDS (5.20 ml, 24.69 mmol), ClSiMe$_3$ (3.10 ml, 24.69 mmol), and SnCl$_4$ (4.30 ml, 37.04 mmol). The resulting clear solution was refluxed for one hour. Then the solvent was evaporated and the residue was dissolved in EtOAc (750 ml), washed with H$_2$O, and saturated NaHCO$_3$ solution. The EtOAc layer was dried over sodium sulfate, filtered and evaporated to give the crude product. This crude product was purified on a silica gel column using 40–50% EtOAc/petroleum ether to give pure 3 (11.7 g, 66.0% yield) as a white foam.

NMR: (CDCl$_3$) δ=4.65 (dd, 1H), 4.78 (dd, 1H), 4.97 (dd, 1H, 5.75–5.88 (2 t, 2H), 6.27 (d, 1H), 7.36–7.62 and 8.00–8.10 (m, 5H), 8.94 (d, 1H).

1-α-L-arabinofuranosyl-5-fluorouracil (4)

To a solution of compound 3 (11.7 g, 20.37 mmol) in MeOH (300 ml), NaOMe (4.2 ml of a methanolic 25% w/v solution) was added and the solution was stirred until the reaction was complete. The solvent was then evaporated and the residue was dissolved in H$_2$O (200 ml), washed with ether and neutralized with Dowex 50 ion exchange resin. After filtration of the resin, the aqueous solution was evaporated to give compound 4 (4.92 g, 92% yield) as a white foam.

NMR: (DMSO-d$_6$) δ=3.48 (m, 2H), 3.93–4.00 (2 t, 2H), 4.16 (q, 1H), 5.69 (dd, 1H), 8.03 (d, 1H).

1-[3',5'-O-(1,1,3,3-tetraisopropyldisiloxane-1,3-diyl)-α-L-arabinofuranosyl]-5-fluorouracil (5)

To a stirred suspension of 4 (6.43 g, 24.52 mmol) in pyridine (200 ml) was added 1,3-dichloro-1,1,3,3-tetraisopropyldisiloxane (10.3 ml, 29.43 mmol). This was stirred at room temperature until the reaction was complete (5 hours). The solvent was evaporated to a residue which was dissolved in EtOAC and washed successively with H$_2$O, 5% HCl, H$_2$O, saturated NaHCO$_3$, and brine. After drying the EtOAc portion over Na$_2$SO$_4$, the solution was filtered and evaporated to give the crude product 5 which was used in the next step without further purification.

1-[2'-O-phenoxythiocarbonyl-3',5'-O-(1,1,3,3-tetraisopropyldisiloxane-1,3-diyl)-α-L-arabinofuraosyl]-5-fluorouracil (6)

To a solution of 5 (24.52 mmol) in anhydrous MeCN (300 ml) were added 4-dimethylaminopyridine (DMAP) (5.80 g, 47.58 mmol), and phenylchlorothionoformate (3.85 ml, 26.98 mmol). The solution was stirred at room temperature for 24 hours. Then, the solvent was evaporated to a residue which was dissolved in EtOAc and washed successively with H$_2$O, 5% HCl, H$_2$O, saturated NaHCO$_3$, and brine. After drying the EtOAc portion over Na$_2$SO$_4$, the solution was filtered and evaporated to an oil. The oil was purified on a silica gel column using 30% EtOAc/petroleum ether to produce pure 6 (8.9 g, 56.7% yield) as a yellow foam.

NMR: (CDCl$_3$) δ=4.02 (m, 2H), 4.32 (m, 1H), 4.76 (dd, 1H), 6.10 (dd, 1H), 6.18 (dd, 1H), 7.07–7.48 (m, 6H), 8.41 (br s, 1H).

3',5'-O-(1,1,3,3-tetraisopropyldisiloxane-1,3-diyl)-α-L-2'-deoxy-5-fluorouridine (7)

To a solution of 6 (8.92 g, 13.91 mmol), in dry toluene (300 ml) was added AIBN (0.46 g, 2.78 mmol) followed by Bu$_3$SnH (20.0 ml, 69.35 mmol). The solution was deoxygenated with argon and heated at 75° C. for four hours. The solvent was then evaporated and the residue was purified on a silica gel column using 30% EtOAc/petroleum ether to give pure 7 (5.44 g, 80% yield) as a white foam.

NMR: (CDCl$_3$) δ=2.16 (m, 1H), 2.84 (m, 1H), 3.8 Cm, 1H), 4.07 (m, 1H), 4.60 (m, 1H), 6.19 (ddd, 1H), 7.92 (m, 1H).

2'-deoxy-α-L-5-fluorouridine (8)

A solution of compound 7 (5.44 g, 11.13 mmol) and NH$_4$F (4.12 g, 111.3 mmol) in MeOH was stirred in an oil bath at 60° C. for 3 hours. Silica gel (3 g) was added and the mixture was evaporated to a dry powder. This powder was added to a silica column and eluted with 10–15% MeOH/CHCl₃ to produce pure 8 (2.4 g, 87.6% yield) as a white foam.

NMR: (DMSO-d₆) δ=1.90 (m,1H), 2.55 (m, 1H), 3.33 (m,2H), 4.19 (m, 2H), 4.86 (br s, 1H), 5.43 (br s, 1H), 6.10 (dd, 1H), 8.15 (d, 1H), 11.78 (br s, 1H).

EXAMPLE 2

Synthesis of 2'-deoxy-α-L-uridine 1-(2', '3', 5'-tri-O-benzoyl-α-L-arabinofuranosyl) uracil (9)

To a mixture of uracil (1.17 g, 10.49 mmol) and compound 2 (5 g) in anhydrous MeCN (100 ml) were successively added HMDS (1.77 ml, 8.39 mmol), ClSiMe₃ (1.06 ml, 8.39 mmol), and SnCl₄ (1.47 ml, 12.58 mmol) The resulting clear solution was refluxed for one hour. Then the solvent was evaporated and the residue was dissolved in EtOAc (200 ml), washed with H₂O, and saturated NaHCO₃ solution. The EtOAc layer was dried over sodium sulfate, filtered and evaporated to give the crude product, which was purified on a silica gel column using 40–50% EtOAc/petroleum ether to give pure 9 (3.66 g, 62.7% yield) as a white foam.

NMR: (CDCl₃) δ=4.70 (m, 1H), 5.77 (5, 1H), 5.80 (dd, 1H), 5.94 (t, 1H), 6.20 (d, 1H), 7.40–8.10 (m, 16H), 8.58 (br s, 1H).

1-α-L-arabinofuranosyl-uracil (10)

To a solution of compound 8 (17.83 g, 32.03 mmol) in MeOH (400 ml), NaOMe (5.0 ml of a methanolic 25% w/v solution) was added and the solution was stirred until the reaction was complete. The solvent was then evaporated and the residue was dissolved in H₂O (250 ml), washed with ether and neutralized with Dowex 50 ion exchange resin. After filtration of the resin, the aqueous solution was evaporated to give compound 10 (7.4 g, 94.6% yield) as a white foam. This was used in the next step without further purification.

1-[3',5'-o-(1.1,3,3-tetraisopropyldisiloxane-1,3-diyl)-α-L-arabinofuranosyl]-uracil (11)

To a stirred suspension of 10 (7.4 g, 30.3 mmol) in pyridine was added 1.3-dichloro-1,1,3,3-tetraisopropyldisiloxane (12.74 ml, 36.36 mmol). This was stirred at room temperature until the reaction was complete (5 hours). The solvent was evaporated to a residue which was dissolved in EtOAC (500 ml) and washed successively with H₂O, 5% HCl, H₂O, saturated NaHCO₃, and brine. After drying the EtOAc portion over Na₂SO₄, the solution was filtered and evaporated to give the crude product 11 which was used in the next step without further purification.

1-[2'-o-phenoxythiocarbonyl-3',5'-o-(1,1,3,3-tetraisopropyldisiloxane-1,3-diyl)-α-L-arabinofuranosyl]-uracil (12)

To a solution of 11 (30.3 mmol) in anhydrous MeCN were added 4-dimethylaminopyridine (DMAP) (7.2 g, 58.78 mmol), and phenylchlorothionoformate (4.7 ml, 33.33 mmol). The solution was stirred at room temperature for 24 hours. Then, the solvent was evaporated to a residue which was dissolved in EtOAc (750 ml) and washed successively with H₂O, 5% HCl, H2O, saturated NaHCO₃, and brine. After drying the EtOAc portion over Na₂SO₄, the solution was filtered and evaporated to an oil. The oil was purified on a silica gel column using 30% EtOAc/petroleum ether to produce pure 12 (13.14 g, 74.5% yield) as a white foam.

NMR: (CDCl₃) δ=4.04 (m, 2H), 4.38 (m, 1H), 4.73 (dd, 1H), 5.79 (dd, 1H), 5.93 (d, 1H), 6.31 (dd, 1H), 7.08–7.33 (m, 6H), 9.2 (br s, 1H).

3',5'-o-(1,1,3,3-tetraisopropyldisiloxane-1,3-diyl)-α-L-2'-deoxyuridine (13)

To a mixture of 12 (13.14 g, 21.09 mmol), in dry toluene (300 ml) was added AIBN (0.69 g, 4.2 mmol) followed by Bu₃SnH (28.4 ml, 105.4 mmol). The solution was deoxygenated with argon and heated at 75° C. for four hours. The solvent was then evaporated and the residue was purified on a silica gel column using 30% EtOAc/petroleum ether to give pure 13 (9.29 g, 88.4% yield) as a white foam.

NMR: (CDCl₃) δ=2.15 (2 t, 1H), 2.81 (m, 1H), 3.82 (dd, 1H), 4.05 (m, 2H), 4.56 (q, 1H), 5.75 (dd, 1H), 6.16 (t, 1H), 7.69 (d, 1H), 9.38 (br s, 1H).

2'-deoxy-α-L-uridine (14)

A mixture of compound 13 (9.2 g, 18.63 mmol) and NH₄F (6.9 g, 186.3 mmol) in MeOH (200 ml) was stirred in an oil bath at 60° C. for 3 hours. Silica gel (5 g.) was added and the mixture was evaporated to a dry powder. This powder was added to a silica column and eluted with 10–15% MeOH/CHCl₃ to produce pure 14 (3.70 g, 83% yield) as a white foam.

NMR: (DMSO-d₆) δ=1.87 (m, 1H), 2.56 (m, 1H), 3.41 (m, 2H), 4.15 (m, 1H), 4.22 (m, 1H), 4.44 (t, 1H), 4.92 (t, 1H), 5.38 (d, 1H), 5.62 (d, 1H), 6.09 (dd, 1H).

EXAMPLE 3

Synthesis of 2'-deoxy-α-L-cytidine

3',5'-di-O-benzoyl-2'-deoxy-α-L-uridine (15)

A solution of BzCN (0.61 g, 4.67 mmol) in MeCN (10 ml) was added dropwise to a suspension of compound 14 (0.43 g, 1.87 mmol) in MeCN (10 ml) followed by Et₃N (0.1 ml). The reaction was stirred at room temperature for three hours after which time the solvent was evaporated to dryness. The crude material was purified on a silica gel column using 50% EtOAc/petroleum ether to give pure 15 (0.57 g, 70% yield) as yellow foam.

NMR: (CDCl₃) δ=2.55 (d, 1H), 2.96 (dt, 1H), 4.56 (m, 2H), 4.86 (t, 1H), 5.61 (d, 1H), 5.73 (dd, 1H), 6.31 (dd, 1H), 7.40–7.63 (m, 7H), 7.87–8.06 (m, 4H), 8.82 (br s, 1H).

3',5'-di-O-benzoyl-2'-deoxy-4-thio-α-L-uridine (16)

A boiling solution of compound 15 (0.54 g, 1.25 mmol) in anhydrous dioxane was treated with PzS₅ (0.61 g, 2.75 mmol) and the mixture was refluxed under a nitrogen atmosphere for one hour. Remaining solids were filtered from the hot solution and washed on the filter with additional dioxane. The filtrate was evaporated to dryness and the crude product was purified on a silica gel column using 30% EtOAc/petroleum ether to give pure 16 (0.42 g, 74% yield) as a yellow oil.

NMR: (CDCl₃) δ=2.59 (d, 1H), 2.93 (dt, 1H), 4.58 (m, 2H), 4.89 (t, 1H), 5.63 (d, 1H), 6.26 (dd, 1H), 6.41 (dd, 1H), 7.40–8.10 (m, 11H), 9.54 (br s, 1H).

2'-deoxy-α-L-cytidine (17)

Compound 16 (0.42 g, 9.28 mmol) was treated with NH₃/MeOH (50 ml) in a steel bomb at 100° C. for 10 hours. After cooling, the solvent was evaporated to dryness, the residue was dissolved in water (50 ml) and washed with ether (3×50 ml). The water layer was treated with charcoal, filtered through Celite and evaporated to dryness by coevaporation with EtOH. The semi-solid obtained was crystallized from EtOH/ether to give compound 17 (0.18 g, 85.7% yield).

NMR: (DMSO-d₆) δ=1.86 (Cd,H), 2.50 (m, 1H), 3.40 (m, 1H), 4.12 (m, 1H), 4.15 (m, 1H), 4.86 (t, 1H), 5.21 (d, 1H), 5.69 (d, 1H), 6.03 (dd, 1H), 7.02 (br d, 1H), 7.74 (d, 1H).

N⁴-benzoyl-2'-deoxy-α-L-cytidine (18)

ClSiMe₃ (2.3 ml, 18.05 mmol) was added dropwise over 30 minutes to a stirring suspension of compound 17 (0.82 g, 3.61 mmol) in pyridine (50 ml) chilled in an ice bath. BzCl (2.1 ml, 18.05 mmol) was then added dropwise and the reaction mixture was cooled at room temperature for two hours. The reaction mixture was again cooled in an ice bath and cold water (10 ml) was added dropwise. Fifteen minutes later, concentrated NH$_4$OH (10 ml) was added to produce a solution of ammonia of a concentration of about 2M. Thirty minutes after the addition of the ammonia solution, a solvent was evaporated, dissolved in water and washed with ether. Evaporation of this aqueous solution provided the crude product (18) which was used in the next step without further purification.

EXAMPLE 4

Synthesis of Dimers

The dimers were prepared from the monomeric materials by the general scheme shown in Scheme 2.

A. α-L, β-D 5 FUdR Dimer

5'-O-dimethoxytrityl-α-L-5-fluoro-2'-deoxyuridine (20a)

α-L-5-fluoro-2'-deoxyuridine (8) (500 mg, 2.0 mmol) was dissolved in 10 ml of dry, distilled pyridine. To this solution was added 4,4'-dimethoxytrityl chloride (813 mg, 2.4 mmol) and 4-dimethylaminopyridine (DMAP) (50 mg, 0.4 mmol). The mixture was stirred under an argon atmosphere for 16 hours. After this time, the pyridine was stripped off in vacuo. The residue was dissolved in EtOAc (50 ml). The organic layer was washed with saturated NaHCO$_3$, water and with brine. The organic layer was dried over Na$_2$SO$_4$, filtered and evaporated in vacuo to a residue which was purified on a silica gel column using 10% MeOH/CHCl$_3$. Pure fractions were pooled and evaporated to give the pure product as an off-white foam (679 mg, 86% yield). Rf=0.48 in 10% MeOH/CHCl$_3$.

NMR: (DMSO-d$_6$) δ=2.3 (dd, 1H), 2.72–2.81 (m, 1H), 3.15–3.26 (m, 2H), 3.75 (s, 6H), 4.45 (m, 2H), 6.23 (dd, 1H), 6.92 (d, 1H), 7.2–7.3 (m, 13 H), 7.94 (d, 1H).

5'-O-dimethoxytrityl-α-L-5-fluoro-2'-deoxyuridine-3'-N,N-diisopropylmethoxy phosphoramidite (21a)

The 5'-O-dimethoxytrityl-α-L-5-fluoro-2'-deoxyuridine (20a, 548 mg, 1 mmol) was dissolved in anhydrous dichloromethane (20 ml). N,N-diisopropylethylamine (700 μl, 4 mmol) was added through a septum, followed by chloro-N,N-diisopropylmethoxyphosphine (290 μl, 1.5 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10; Rf=0.69). The product (390 mg) was isolated as a yellow foam and it was used in the next step without further purification.

3'-Acetoxy-β-D-5-fluoro-2'-deoxyuridine (24a)

β-D-5-fluoro-2'-deoxyuridine (500 mg, 2.2 mmol) was dissolved in 10 ml of dry, distilled pyridine. To this solution was added 4,4'-dimethoxytrityl chloride (813 mg, 2.4 mmole) and 4-dimethylaminopyridine (DMAP) (50 mg, 0.4 mmole). The mixture was stirred at room temperature for 16 hours. The pyridine was stripped off in vacuo. The residue was dissolved in dichloromethane (50 ml). The organic layer was washed with 0.3 N HCl, brine, saturated NaHCO$_3$, and again with brine. The organic layer was dried over Na$_2$SO$_4$, filtered and evaporated in vacuo to a residue which was purified on a silica gel column, eluting with 10% MeOH/CHCl$_3$. Pure fractions were pooled and evaporated to give the pure product as an off-white foam (685 mg, 86% yield). This material was dissolved in pyridine (12 ml) and treated with acetic anhydride (2.5 ml) for 3 hours at room temperature. The solvent was evaporated, and the residue was dissolved in ethyl acetate. The ethyl acetate was washed as described above, dried over sodium sulfate and evaporated. The residue was then treated with 80% acetic acid (10 ml) for 2.5 hours at room temperature. The solvent was evaporated in vacuo and the residue was chromatographed on silica gel, eluting with 10% MeOH/CHCl$_3$ to give pure 24a as a white foam, yield 422 mg.

NMR: (DMSO-d$_6$) δ=1.95 (s, 3H), 2.08–2.24 (m, 2H), 3.65–3.9 (m, 2H), 4.45 (m, 1H), 4.72 (m, 1H), 6.24 (dd, 1H), 8.24 (d, 1H).

5'-O-dimethoxytrityl-3'-[o-(3'-O-acetyl)-β-D-5-fluoro-2'-deoxyuridinyl]-α-L-5-fluoro-2'-deoxyuridine (25a)

The 3'-O-acetyl-β-D-5-fluoro-2'-deoxyuridine (188 mg, 0.65 mmol) was dissolved in dry acetonitrile (5 ml). Sublimed 1H-tetrazole (80 mg) was added and the mixture was stirred under an argon atmosphere for 15 minutes. The solution of 21a (380 mg, 0.54 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (468 mg). This foam was used in the next step without further purification.

(3'-acetoxy-β-D-5-fluoro-2'-deoxyuridinyl)-α-L-5-fluoro-2'-deoxyuridine methyl phosphonate ester (26a)

The dimer, 25a (504 mg), was dissolved in 8 ml of THF and 2 ml of pyridine containing 0.2 ml of water. Iodine crystals (26 mg) were added and the contents of the loosely stoppered flask were allowed to stir for 2.1 hours. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (530 mg) was dissolved in 10 ml of 80% acetic acid/water solution and was stirred until the reaction was completed. The solvent was evaporated and the residue was purified on a silica gel column, using 20% MeOH/CHCl$_3$. Fractions containing one spot by TLC (10% MeOH/CHCl$_3$ Rf=0.35) were pooled and evaporated to give the pure product (316 mg).

NMR: (CD$_3$OD) δ=2.08 (s, 3H), 2.25–2.45 (m, 3H), 2.65–2.72 (m, 1H), 3.60 (m, 2H), 3.80 (2d, 3H), 4.18 (m, 1H), 4.28 (m, 1H), 4.35 (dd, 1H), 4.62 (dd, 1H), 5.05 (dd, 1H), 5.23 (m, 1H), 6.13 (m, 1H), 6.18 (m, 1H), 7.85 (m, 2H).

P$^{31}$ NMR: (CD$_3$OD) δ=0.77 (s), 1.16 (s)

3'-O-(β-D-5-fluoro-2'-deoxyuridinyl)-α-L-5-fluoro-2'-deoxyuridine (27a)

The O-protected dimer, 26a (280 mg) was treated with 20 ml of saturated methanolic ammonia at room temperature until the reaction was completed at room temperature. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (162 mg).

NMR: (D$_2$O) δ=2.2–2.4 (m, 3H), 2.65–2.71 (m, 1H), 3.65 (m, 2H), 4.01 (m, 1H), 4.11 (t, 1H), 4.45 (m, 1H), 4.65 (t, 1H), 6.14 (d, 1H), 6.24 (td, 1H), 8.06 (d, 1H), 8.02 (d, 1H).

$^{31}$P NMR: (D$_2$O) δ=0.04 (s).

B. β-D, α-L 5FUdR Dimer

5'-O-dimethoxytrityl-3'-[O-(3'-O-acetyl)-α-L-5-fluoro-2'-deoxyuridinyl]-β-D-5-fluoro-2'-deoxyuridine (25b)

The 3'-O-acetyl-α-L-5-fluoro-2'-deoxyuridine, 24b (188 mg, 0.65 mmol) was dissolved in dry acetonitrile (5 ml). Sublimed 1H-tetrazole (80 mg) was added and the mixture was stirred under an argon atmosphere for 15 minutes. The solution of 21b (380 mg, 0.54 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (484 mg). This foam was used in the next step without further purification.

(3'-acetoxy-α-L-5-fluoro-2'-deoxyuridinyl)-β-D-5-fluoro-2'-deoxyuridine methyl phosphate ester (26b)

The dimer, 25b (526 mg), was dissolved in 8 ml of THF and 2 ml of pyridine containing 0.2 ml of water. Iodine crystals (26 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated $NaHCO_3$ solution and brine. The organic layer was dried over $Na_2SO_4$, filtered and evaporated in vacuo. The residue (578 mg) was dissolved in 10 ml of 80% acetic acid/water solution and was stirred for three hours. The solvent was evaporated and the residue was purified on a silica gel column, using 10–15% MeOH/$CHCl_3$. Fractions containing one spot by TLC (10% MeOH/$CHCl_3$ Rf–0.35) were pooled and evaporated to give the pure product (342 mg).

NMR: (DMSO-$d_6$) δ=1.98 (s, 3H), 2.2–2.4 (m, 3H), 2.62–2.71 (m, 1H), 3.5–3.8 (m, 4H), 4.02 (m, 1H), 4.42 (m, 2H), 6.10 (dd, 1H), 6.26 (dt, 1H), 8.00 (d, 1H), 8.04 (d, 1H).

3'-O-(α-L-5-fluoro-2'-deoxyuridinyl)-β-D-5-fluoro-2'-deoxyuridine (27b)

The O-protected dimer, 26b (170 mg) was treated with 20 ml of saturated methanolic ammonia at room temperature until the reaction was completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (89 mg).

NMR: ($D_2O$) δ=2.2–2.4 (m, 3H), 2.65–2.71 (m, 1H), 3.54–3.85 (m, 5H), 4.05 (t, 1H), 4.42 (m, 2H), 6.06 (dd, 1H), 6.23 (dt, 1H), 8.00 (d, 1H), 8.04 (d, 1H).

C. α-L uridine, β-D 5 FUdR dimer

5'-O-(di-p-methoxytrityl)-2'-deoxy-α-L-uridine (20c)

α-L-2'-deoxyuridine (1.5 g, 6.57 mmol) was dissolved in 25 ml of dry, distilled pyridine. To this solution was added 4,4'-dimethoxytrityl chloride (2.9 g, 7.89 mmol) and 4-dimethylamino pyridine (DMAP) (160 mg, 1.31 mmol). The mixture was stirred under an argon atmosphere for 16 hours. After this time, the pyridine was stripped off in vacuo. The residue was dissolved in EtOAc (150 ml). The organic layer was washed with saturated $NaHCO_3$. water and again with brine. The organic layer was dried over $Na_2SO_4$, filtered and evaporated in vacuo to a residue which was purified on a silica gel column using 5% MeOH/$CHCl_3$. Pure fractions were pooled and evaporated to give the pure product as an off-white foam (2.84 g, 81% yield).

NMR: ($CDCl_3$-$d_6$) δ=2.29 (d, 1H), 2.70 (m, 2H), 3.17 (m, 2H), 3.78 (s, 6H), 4.44 (m, 2H), 5.63 (d, 1H), 6.19 (d, 1H), 6.83 (d, 4H), 7.28 (m, 9 H), 7.68 (d, 1H), 9.30 (br s, 1H).

5'-O-(dimethoxytrityl)-α-L-2'-deoxyuridine-3'-N,N-diisopropylmethoxy phosphoramidite (21c)

The 5'-O-dimethoxytrityl-α-L-2'-deoxyuridine (2.35 g, 4.43 mmol) was dissolved in anhydrous dichloromethane (50 ml). N,N-diisopropylethylamine (3.1 ml, 17.72 mmol) was added through a septum, followed by chloro-N,N-diisopropylmethoxyphosphine (1.3 ml, 6.64 mmol), under an argon atmosphere. The reaction was stirred for 30 minutes. The solvent was evaporated and the residue was partitioned between an 80% EtOAc/triethylamine mixture and brine. The organic layer was washed with saturated $NaHCO_3$ solution and brine. The organic residue was evaporated to dryness and the residue was purified on a silica gel column using a mixture of dichloromethane, EtOAc and triethylamine (40:50:10; Rf=0.69). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-2'-deoxy-α-L-uridine (25c)

The 3'-O-acetyl-β-D-5-fluoro-2'-deoxyuridine (0.95 g, 3.29 mmol) was dissolved in dry acetonitrile (125 ml). Sublimed 1H-tetrazole (350 mg, 4.91) was added and the mixture was stirred under an argon atmosphere for 15 minutes. The solution of 21c (4.91 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This compound was further purified on a silica gel column using 5% MeOH/$CHCl_3$ to give the pure product (2.81 g, 97% yield).

3'-acetoxy-β-D-5'-fluoro-2'-deoxyuridinyl)-α-L-2'-deoxyuridine methyl phosphate ester (26c)

The dimer, 25c (2.81 g, 3.2 mmol), was dissolved in a mixture of THF:pyridine:water (25:6:0.6). Iodine crystals (150 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated $NaHCO_3$ solution and brine. The organic layer was dried over $Na_2SO_4$, filtered and evaporated in vacuo. The residue (1.48 g) was dissolved in 25 ml of 80% acetic acid/water solution and was stirred until the reaction was completed. The solvent was evaporated and the residue was purified on a silica gel column, using 10% MeOH/$CHCl_3$. Fractions containing one spot by TLC (10% MeOH/$CHCl_3$ Rf=0.4) were pooled and evaporated to give the pure product (0.465 g, 25% yield).

NMR: ($CD_3OD$) δ=2.09 (d, 3H), 2.40 (m, 3H), 2.80 (m, 1H), 3.78 (dd, 3H), 4.30 (m, 3H), 4.63 (m, 1H), 5.05 (m, 1H), 5.23 (m, 1H), 5.70 (d, 1H), 6.13 (m, 1H), 6.20 (m, 1H), 7.73 (d, 1H), 7.82 (d, 1H).

$P^{31}$ NMR: ($CD_3OD$) δ=0.56 (s), 0.84 (s).

3'-O-(β-D-5-fluoro-2'-deoxyuridinyl)-α-L-2'-deoxyuridine (27c)

The O-protected dimer, 26c (465 mg, 0.78 mmol) was treated with 50 ml of saturated methanolic ammonia at room temperature until the reaction was completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (370 mg, 87.7% yield).

NMR: ($CD_3OD$) δ=2.23 (m, 2H), 2.29 (d, 1H), 2.73 (m, 1H), 4.0 (d, 2H), 4.42 (m, 1H), 4.56 (m, 1H), 4.81 (m, 1H), 5.69 (d, 1H), 6.24 (m, 2H), 7.85 (d, 1H), 8.02 (d, 1H).

$P^{31}$ NMR: ($CD_3OD$) δ=1.25 (s).

D. β-L, β-L 5 FUdR dimer

5'-O-dimethoxytrityl-β-L-5-fluoro-2'-deoxyuridine (20d)

β-L-5-fluoro-2'-deoxyuridine (19d, 1.42 g, 5.77 mmol) was dissolved in 25 ml of dry, distilled pyridine. To this solution was added 4,4'-dimethoxytrityl chloride (2.34 g, 6.92 mmol) and 4-dimethylamino pyridine (DMAP) (140 mg, 1.15 mmol). The mixture was stirred under an argon atmosphere for 16 hours. After this time, the pyridine was stripped off in vacuo. The residue was dissolved in EtOAc (100 ml). The organic layer was washed with saturated NaHCO$_3$, and with brine. The organic layer was dried over Na$_2$SO$_4$, filtered and evaporated in vacuo to a residue which was purified on a silica gel column using 5% MeOH/CHCl$_3$. Pure fractions were pooled and evaporated to give the pure product as an off-white foam (2.88 g, 88.7% yield).

NMR: (CDCl$_3$) δ=2.25 (m, 1H), 2.50 (m, 1H), 3.50 (m, 2H), 3.80 (s, 6H), 4.08 (m, 1H), 4.58 (m, 1H), 6.30 (t, 1H), 6.84 (d, 4H), 7.28 (m, 9 H), 7.82 (d, 1H), 8.58 (br s, 1H).

5'-O-dimethoxytrityl-β-L-5-fluoro-2'-deoxyuridine-3'-N,N-diisopropylmethoxy phosphoramidite (21d)

The 5'-O-dimethoxytrityl-p-L-5-fluoro-2'-deoxyuridine (20d, 840 mg, 1.53 mmol) was dissolved in anhydrous dichloromethane (50 ml). N,N-diisopropylethylamine (1.1 ml, 6.13 mmol) was added through a septum, followed by chloro-N,N-diisopropylmethoxyphosphine (0.42 ml, 2.3 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (45:45:10; Rf=0.69). The product (700 mg, 65%) was isolated as a yellow foam and it was used in the next step without further purification.

5'-O-dimethoxytrityl-3'-[O-(3'-O-acetyl)-β-L-5-fluoro-2'-deoxyuridinyl]-β-L-5-fluoro-2'-deoxyuridine (25d)

The 3'-acetyl-β-L-5-deoxyuridine, 24d (330 mg, 1.15 mmol) was dissolved in dry acetonitrile (50 ml). Sublimed 1H-tetrazole (120 mg, 1.77 mmol) was added and the mixture was stirred under an argon atmosphere for 15 minutes. The solution of 21d (950 mg, 1.36 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This foam was purified on a silica gel column using 5% MeOH/CHCl$_3$ to give the pure product (960 mg, 93% yield).

NMR: (CDCl$_3$) δ=2.10 (d, 3H), 2.28 (m, 2H), 2.49 (m, 2H), 3.42 (m, 3H), 3.51 (dd, 3H), 3.76 (s, 6H), 4.07 (m, 1H), 4.55 (m, 1H), 4.87 (m, 1H), 5.23 (m, 1H), 6.30 (m, 2H), 6.84 (d, 4H), 7.30 (m, 9H), 7.82 (m, 2H).

(3'-acetoxy-β-L-5-fluoro-2'-deoxyuridinyl)-β-L-5-fluoro-2'-deoxyuridine methyl phosphate ester (26d)

The dimer, 25d (960 mg, 1.07 mmol), was dissolved in a mixture containing THF:pyridine:water (12:3:0.3). Iodine crystals (50 mg) were added and the contents of the loosely stoppered flask were allowed to stir for 1 hour. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue (530 mg) was dissolved in 20 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (310 mg, 46% yield).

NMR: (CD$_3$OD) δ=2.08 (s, 3H), 2.35–2.54 (m, 4H), 3.79 (m, 2H), 3.83 (dd, 3H), 4.18 (m, 2H), 5.08 (m, 1H), 5.29 (m, 1H), 6.24 (m, 1H), 7.86 (dd, 1H), 8.19 (dd, 1H).

P$^{31}$ NMR: (CD$_3$OD) δ=0.82 (s), 1.03 (s).

3'-O-(-L-5-fluoro-2'-deoxyuridinyl)-β-L-5-fluoro-2'-deoxyuridine (27d)

The O-protected dimer, 26d (300 mg, 0.49 mmol) was treated with 50 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (240 mg, 85% yield).

NMR: (CD$_3$OD) δ=2.25 (m, 3H), 2.50 (m, 1H), 3.79 (d, 2H), 4.03 (m, 1H), 4.08 (m, 2H), 4.18 (m, 1H), 4.44 (m, 1H), 4.90 (m, 1H), 6.25 (t, 1H), 8.01 (d, 1H), 8.24 (d, 1H).

P$^{31}$ NMR: (CD$_3$OD) δ=0.18 (s).

E. β-L, β-D 5 FUdR dimer

5'-O-dimethoxytrityl-3'-[O-(3'-O-acetyl)-β-D-5-fluoro-2'-deoxyuridinyl]-β-L-5-fluoro-2'-deoxyuridine (25e)

The 3'-O-acetyl-β-D-5-fluoro-2'-deoxyuridine (250 mg, 0.97 mmol) was dissolved in dry acetonitrile (50 ml). Sublimed 1H-tetrazole (100 mg, 1.46 mmol) was added and the mixture was stirred under an argon atmosphere for 15 minutes. The solution of 21e (1.02 g, 1.46 mmol), dissolved in 5 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam. This foam was purified on a silica gel column using 5% MeOH/CHCl$_3$ to give the pure product quantitatively.

(3'-acetoxy-β-D-5-fluoro-2'-deoxyuridinyl)-β-L-5-fluoro-2'-deoxyuridine methyl phosphonate ester (26e)

The dimer in reduced form, 25 (700 mg, 0.78 mmol), was dissolved in a mixture containing THF:pyridine:water (25:6:0.6). Iodine crystals (100 mg) were added and the contents of the loosely stoppered flask were allowed to stir for 2.5 hours. Excess iodine was discharged by the addition of a few drops of saturated sodium thiosulfate. The reaction mixture was then evaporated to dryness. The crude product was dissolved in EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10% MeOH/CHCl$_3$. Fractions containing one spot by TLC (10% MeOH/CHCl$_3$ Rf=0.35) were pooled and evaporated to give the pure product (340 mg, 71.4% yield).

NMR: (DMSO-d$_6$) δ=2.06 (s, 3H), 2.37 (m, 4H), 3.45 (m, 2H), 3.65 (d, 3H), 4.20 (m, 3H), 4.95 (m, 1H), 5.30 (m, 1H), 5.96 (m, 1H), 6.15 (t, 2H), 7.99 (d, 1H), 8.16 (d, 1H), 11.90(br s, 2H).

NMR: (DMSO-d$_6$) δ=1.93 (s), 2.01 (s).

3'-O-(β-D-5-fluoro-2'-deoxyuridinyl)-β-L-5-fluoro-2'-deoxyuridine (27e)

The O-protected dimer, 26e (340 mg, 0.57 mmol) was treated with 100 ml of saturated methanolic ammonia at room temperature until the reaction was completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (200 mg, 66.9% yield).

NMR: (CD$_3$OD) δ=2.20 (m, 3H), 2.53 (m, 1H), 3.79 (d, 2H), 4.05 (m, 3H), 4.16 (m, 1H), 4.45 (m, 1H), 6.27 (t, 2H), 8.01 (d, 1H), 8.04 (d, 1H), 8.26 (d, 1H).

5'-O-(dimethoxytrityl)-α-L-5-fluoro-2'-deoxyuridine-3'-N,N-diisopropylcyanoethyl phosphoramidite (21f)

The 5'-o-dimethoxytrityl-α-L-5-fluoro-2'-deoxyuridine (1.48 g, 2.71 mmol) was dissolved in anhydrous dichloromethane (50 ml). N,N-diisopropylethylamine (1.9 ml, 10.84 mmol) was added through a septum, followed by 2'-cyanoethyl-N,N-diisopropylchlorophosphoramidite (0.78 ml, 3.52 mmol), under an argon atmosphere. The reaction was stirred for 30 minutes. The solvent was evaporated and the residue was partitioned between an 80% EtOAc/triethylamine mixture and brine. The organic layer was washed with saturated $NaHCO_3$ solution and brine. The organic residue was evaporated to dryness and the residue was purified on a silica gel column using a mixture of dichloromethane, EtOAc and triethylamine (45:45:10:Rf=0.7). The product was isolated quantitatively as a yellow foam and it was used in the next step without further purification.

5'-O-dimethoxytrityl-3'-[O-(5'-O-dimethoxytrityl)-β-D-5-fluoro-2'-deoxyuridinyl]-α-L-5-fluoro-2'-deoxyuridine (25f)

The 5'-O-dimethoxytrityl-β-D-5-fluoro-2'-deoxyuridine (0.44 g, 0.81 mmol) was dissolved in dry acetonitrile (20 ml). Sublimed 1H-tetrazole (90 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (970 mg). This foam was used in the next step without further purification.

(β-D-5-fluoro-2'-deoxyuridinyl)-α-L-5-fluoro-2'-deoxyuridine cyanoethyl phosphonate ester (26f)

The dimer, 25f (970 mg), was dissolved in 16 ml of THF and 4 ml of pyridine containing 0.4 ml of water. Iodine crystals (50 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/CHCL3. Fractions containing one spot by TLC (10% MeOH/$CHCL_3$ Rf=0.35) were pooled and evaporated to give the pure product (330 mg).

3'-O-(β-D-5-fluoro-2'-deoxyuridinyl)-α-L-5-fluoro-2'-deoxyuridine (27f)

The O-protected dimer, 26f (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (79 mg).

NMR: ($CD_3OD$) δ=2.45 (m, 3H), 2.69 (m, 1H), 3.67 (m, 2H), 3.76 (m, 2H), 4.13 (t, 1H), 4.65 (m, 2H), 6.19 (m, 2H), 7.98 (td, 2H).

$P^{31}$ NMR: ($D_2O$) δ=−1.0(s).

5'-O-dimethoxytrityl-3'-[O-(3'-O-acetyl)-β-L-5-fluoro-2'-deoxyuridinyl]-α-L-5-fluoro-2'-deoxyuridine (25g)

The 3'-O-acetyl-β-D-5-fluoro-2'-deoxyuridine (0.19 g, 0.67 mmol) was dissolved in dry acetonitrile (20 ml). Sublimed 1H-tetrazole (70 mg) was added and the mixture was stirred under an argon atmosphere for 15 minutes. The solution of 21f (0.51 mg, 0.67 mmol), dissolved in 10 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (611 mg). This foam was used in the next step without further purification.

(3'-acetoxy-β-L-5-fluoro-2'-deoxyuridinyl)-α-L-5-fluoro-2'-deoxyuridine cyanoethyl phosphonate ester (26a)

The dimer, 25g (611 mg), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 20 ml of 80% acetic acid/water solution and was stirred until the reaction was completed. The solvent was evaporated and the residue was purified on a silica gel column, using 10–15% MeOH/$CHCL_3$. Fractions containing one spot by TLC (10% MeOH/$CHCL_3$ Rf=0.35) were pooled and evaporated to give the pure product (200 mg).

3'-O-(β-L-5-fluoro-2'-deoxyuridinyl)-α-L-5-fluoro-2'-deoxyuridine (27g) [α-L β-L 5FUdR Dimer]

The o-protected dimer, 26g (200 mg) was treated with 20 ml of concentrated ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (134 mg).

NMR: ($D_2O$) δ=2.30 (m, 3H), 2.71 (m, 1H), 3.65 (m, 2H), 4.03 (m, 2H), 4.08 (t, 1H), 4.47 (m, 1H), 4.68 (m, 2H), 6.13 (d, 1H), 6.24 (td, 1H), 7.89 (d, 1H), 7.95 (d, 1H).

$P^{31}$NMR: ($D_2O$) δ=0.32(s).

5'-O-(dimethoxytrityl)-β-L-2'-deoxyuridine-3'-N,N-diisopropylmethoxy phosphoramidite (21h)

The 5'-O-dimethoxytrityl-α-L-2'-deoxyuridine (1.0 g, 1.88 mmol) was dissolved in anhydrous dichloromethane (50 ml). N,N-diisopropylethylamine (1.31 ml, 7.55 mmol) was added through a septum, followed by chloro-N,N-diisopropylmethoxyphosphine (0.55 ml, 2.83 mmol), under an argon atmosphere. The reaction was stirred for 30 minutes. The solvent was evaporated and the residue was partitioned between an 80% EtOAc/triethylamine mixture and brine. The organic layer was washed with saturated $NaHCO_3$ solution and brine. The organic residue was evaporated to dryness and the residue was purified on a silica gel column using a mixture of dichloromethane, EtOAc and triethylamine (50:40:10; Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-β-L-2'-deoxyuridine (25h)

The 3'-O-acetyl-β-D-5-fluoro-2'-deoxyuridine (0.54 g, 1.88 mmol) was dissolved in dry acetonitrile (50 ml). Sublimed 1H-tetrazole (200 mg) was added and the mixture was stirred under an argon atmosphere for 15 minutes. The solution of 21h (1.88 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (1.08 g). This foam was used in the next step without further purification.

(3'-acetoxy-β-D-5-fluoro-2'-deoxyuridinyl)-β-L-2'-deoxyuridine methyl phosphonate ester (26h)

The dimer, 25h (1.08 g), was dissolved in 15 ml of THF and 3 ml of pyridine containing 0.3 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10–15% MeOH/CHCL$_3$. Fractions containing one spot by TLC (10% MeOH/CHCL$_3$ Rf=0.4) were pooled and evaporated to give the pure product (400 mg).

3'-O-(β-D-5-fluoro-2'-deoxyuridinyl)-α-L-2'-deoxyuridine (27h)

The O-protected dimer, 26h (400 mg) was treated with 100 ml of methnolic ammonia solution until the reaction is completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (175 mg).

NMR: (D$_2$O) δ=2.40 (m, 3H), 2.61 (m, 1H), 3.80 (m,2H), 4.10 (m, 2H), 4.18 (m,2H), 4.55 (m, 1H), 4.80 (m, 1H), 5.85 (d, 1H), 6.30 (q, 2H), 7.85 (d, 1H), 8.06 (d, 1H).

P$^{31}$NMR: (D$_2$O) δ=0.20(s).

5'-O-dimethoxytrityl-N$^4$-benzoyl-2'-deoxy-β-L-cytidine (20i)

N$^4$-benzoyl-2'-deoxy-β-L-cytidine (0.8 g, 2.42) was dissolved in 50 ml of dry, distilled pyridine. To this solution was added 4,4'-dimethoxytrityl chloride (3.0 g, 8.85 mmol) and 4-dimethylamino pyridine (DMAP) (60 mg, 0.48 mmol). The mixture was stirred under an argon atmosphere for 16 hours. After this time, the pyridine was stripped off in vacuo. The residue was dissolved in EtOAc (100 ml). The organic layer was washed with water, saturated NaHCO$_3$, and brine. The organic layer was dried over Na$_2$SO$_4$, filtered and evaporated in vacuo to a residue which was purified on a silica gel column using 10% MeOH/CHCl$_3$. Pure fractions were pooled and evaporated to give the pure product as an off-white foam (1.49 g, (97% yield). Rf=0.48 in 10% MeOH/CHCl$_3$.

NMR: (CDCl$_3$-d$_6$) δ=2.3 (m, 1H), 2.75 (m, 2H), 3.42 (ddd, 2H), 3.80 (s, 6H), 4.15 (q, 2H), 4.52 (m, 1H), 6.30 (t, 1H), 6.82 (dd, 4H), 7.2–7.6 (m, Ar), 7.85 (d, 2H), 8.32 (d, 1H), 8.76 (br s, 1H).

5'-O-(dimethoxytrityl)-N$^4$-benzoyl-2'-deoxy-β-L-cytidine-3'-N,N-diisopropylmethyl phosphoramidite (21i)

The 5'-O-dimethoxytrityl-N4-benzoyl-2'-deoxy-β-L-cytidine (0.6 g, 0.95 mmol) was dissolved in anhydrous dichloromethane (50 ml). N,N-diisopropylethylamine (0.66 ml, 3.79 mmol) was added through a septum, followed by chloro-N,N-diisopropylmethoxyphosphine (0.28 ml, 1.42 mmol), under an argon atmosphere. The reaction was stirred for 30 minutes. The solvent was evaporated and the residue was partitioned between an 80% EtOAc/triethylamine mixture and brine. The organic layer was washed with saturated NaHCO$_3$ solution and brine. The organic residue was evaporated to dryness and the residue was purified on a silica gel column using a mixture of dichloromethane, EtOAc and triethylamine (60:30:10;Rf=0.8). The product was isolated quantitatively as a yellow foam and it was used in the next step without further purification.

5'-O-dimethoxytrityl-3'-[O-(3'-O-acetyl)-β-D-5-fluoro-2'-deoxyuridinyl]-N$^4$-benzoyl-2'-deoxy-β-L-cytidine (25i)

The 3'-O-acetyl)-β-D-5-fluoro-2'-deoxyuridine (0.23 g, 0.78 mmol) was dissolved in dry acetonitrile (30 ml). Sublimed 1H-tetrazole (110 mg) was added and the mixture was stirred under an argon atmosphere for 15 minutes. The solution of 21i (0.94 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.73 g). This foam was used in the next step without further purification.

(3'-acetoxy-β-D-5-fluoro-2'-deoxyuridinyl)-N$^4$-benzoyl-2'-deoxy-β-L-cytidine methyl phosphonate ester (26i)

The dimer, 25i (0.73 g), was dissolved in 20 ml of THF and 4 ml of pyridine containing 0.4 ml of water. Iodine crystals (100 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated NaHCO$_3$ solution and brine. The organic layer was dried over Na$_2$SO$_4$, filtered and evaporated in vacuo. The residue was dissolved in 25 ml of 80% acetic acid/water solution and was stirred until the reaction was completed. The solvent was evaporated and the residue was purified on a silica gel column, using 10–15% MeOH/CHCl$_3$. Fractions containing one spot by TLC (10% MeOH/CHCl$_3$ Rf=0.4) were pooled and evaporated to give the pure product (108 mg).

3'-O-(β-D-5-fluoro-2'-deoxyuridinyl)-2'-deoxy-β-L-cytidine (27i)

The O-protected dimer, 26i (108 mg) was treated with 100 ml of methnolic ammonia solution until the reaction is completed. The solvent was stripped off in vacuo and the residue was purified on DEAE cellulose ion exchange column using gradient of NH$_4$CO$_3$ buffer from 0.02–0.2 M. Pure fractions were evaporated at 40° C. in high vacuo to dryness to give the pure product (56 mg).

NMR: (D$_2$O) δ=2.30 (m, 3H), 2.55 (m, 1H), 3.80 (m, 2H), 4.05 (m, 2H), 4.18 (m, 2H), 4.52 (m, 1H), 4.78 (m, 1H), 6.02 (d, 1H), 6.25 (m, 2H), 7.80 (d, 1H), 8.04 (d, 1H).

P$^{31}$NMR: (D$_2$O) δ=0.05(s)

5'-O-dimethoxytrityl-3'-[O-(3'-O-acetyl)-N$^4$-benzoyl-2'-deoxy-β-L-cytidinyl)-β-D-5-fluoro-2'deoxyuridine (25j)

The 3'-O-acetyl-β-D-5-fluoro-2'-deoxyuridine (0.25 g, 0.67 mmol) was dissolved in dry acetonitrile (30 ml). Sublimed 1H-tetrazole (94 mg) was added and the mixture was stirred under an argon atmosphere for 15 minutes. The solution of 21j (0.51 g, 0.67 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.49 g). This foam was used in the next step without further purification.

(3'-acetoxy-N-benzoyl-2'-deoxy-β-L-cytidinyl)-β-D-5-fluoro-2'-deoxyuridinyl cyanoethyl phosphonate ester (26j)

The dimer, 25J (0.49 g), was dissolved in 8 ml of THF and 2 ml of pyridine containing 0.2 ml of water. Iodine crystals (30 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 20 ml of 80% acetic acid/water solution and was stirred until the reaction was completed. The solvent was evaporated and the residue was purified on a silica gel column, using 10–15% $MeOH/CHCl_3$. Fractions containing one spot by TLC (10% $MeOH/CHCl_3$ Rf=0.4) were pooled and evaporated to give the pure product (188 mg).

3'-O-(2'-deoxy-β-L-cytidinyl)-β-D-5-fluoro-2'-deoxyuridine (27j)

The O-protected dimer, 26j (188 mg) was treated with 100 ml of concentrated ammonia solution until the reaction is completed. The solvent was stripped off in vacuo and the residue was purified on DEAE cellulose ion exchange column using gradient of $NH_4CO_3$ buffer from 0.02–0.2 M. Pure fractions were evaporated at 40° C. in high vacuo to dryness to give the pure product (105 mg).

NMR: ($D_2O$) δ=2.30 (m, 3H), 2.50 (m, 1H), 3.80 (m, 2H), 4.05 (m, 2H), 4.10 (m, 2H), 4.20 (m, 1H), 4.52 (m, 1H), 4.75 (m, 1H), 6.05 (d, 1H), 6.29 (q, 2H), 7.89 (d, 1H), 9.03 (d, 1H).

$P^{31}$NMR: ($D_2O$) δ=0.05(s)

5'-O-dimethoxytrityl-3'-[O-(3'-O-acetyl)-$N^4$-benzoyl-2'-deoxy-α-L-cytidinyl)-β-D-5-fluoro-2'-deoxyuridine (25k)

The 3'-O-acetyl-β-D-5-fluoro-2'-deoxyuridine (0.19 g, 0.51 mmol) was dissolved in dry acetonitrile (30 ml). Sublimed 1H-tetrazole (80 mg) was added and the mixture was stirred under an argon atmosphere for 15 minutes. The solution of 21k (0.45 g, 0.61 mmol), dissolved in 15 ml of dry acetonitrile was added via syringe to the reaction solution over 5 minutes. The mixture was allowed to stir at room temperature for three hours. The acetonitrile was evaporated in vacuo to a residue. This residue was triturated with a 70% EtOAc/ether mixture. The undissolved tetrazole was filtered off and the filtrate was evaporated to give a dry yellow foam (0.42 g). This foam was used in the next step without further purification.

(3'-acetoxy-$N^4$-benzoyl-2'-deoxy-α-L-cytidinyl)-β-D-5-fluoro-2'-deoxyuridinyl cyanoethyl phosphonate ester (26k)

The dimer, 25k (0.42 g), was dissolved in 10 ml of THF and 2 ml of pyridine containing 0.2 ml of water. Iodine crystals (45 mg) were added and the contents of the loosely stoppered flask were allowed to stir for 1 hour. Excess iodine was discharged by the addition of few drops of saturated sodium thiosulfate. The reaction mixture was then evaporated to dryness. The crude product was EtOAc washed with saturated $NaHCO_3$ solution and brine. The organic layer was dried over $Na_2SO_4$, filtered and evaporated in vacuo. The residue was dissolved in 25 ml of 80% acetic acid/water solution and was stirred until the reaction was completed. The solvent was evaporated and the residue was purified on a silica gel column, using 10–15% $MeOH/CHCl_3$. Fractions containing one spot by TLC (10% $MeOH/CHCl_3$ Rf=0.4) were pooled and evaporated to give the pure product (125 mg).

3'-O-(2'-deoxy-α-L-cytidinyl)-β-D-5-fluoro-2'-deoxyuridine (27k)

The O-protected dimer, 26k (125 mg) was treated with 100 ml of concentrated ammonia solution until the reaction is completed. The solvent was stripped off in vacuo and the residue was purified on DEAE cellulose ion exchange column using gradient of $NH_4CO_3$ buffer from 0.02–0.2 M). Pure fractions were evaporated at 40° C. in high vacuo to dryness to give the pure product (40 mg).

NMR: ($D_2O$) δ=2.15 (m, 1H), 2.35 (m, 1H), 2.60 (m, 1H), 2.71 (m, 1H), 3.81 (m, 2H), 3.97 (m, 2H), 4.22 (m, 1H), 4.52 (m, 2H), 6.02 (d, 1H), 6.15 (dd, 1H), 6.28 (t, 1H), 7.87 (d, 1H), 8.03 (d, 1H).

$P^{31}$NMR: ($D_2O$) δ=0.12(s).

EXAMPLE 5

Dimers Testing In Vitro in B16 Melanoma and P388 Leukemia and in Inhibition Assays Against 293 Processive Telomerase The biological effects of the dimers were compared with those of the monomeric 5-FUdR on P388 leukemia and B16 melanoma cell lines and in inhibition assays against 293 processive telomerase. Telomerase is a DNA-processive enzyme that is not expressed in normal somatic cells but generally only in germ-line cells and fetal cells. In many types of cancer cells, enzyme activity is reactivated, and others, telomerase inhibitors can therefore serve as a valuable new class of antineoplastic agents. The results are shown in Table 2.

TABLE 1

Inhibition of Tumor Cell Growth and Telomerase Activity by 5-FUdR Dinucleoside Monophosphates

| Compound | Growth Inhibition $IC_{50}$ (nM) | | Telomerase Inhibition (Mean ± SEM) |
|---|---|---|---|
| | P388 | B16 | % at 1 mN |
| β-D FUDR | 2.8 | 28 | 0 |
| α-L, β-D Dimer | 0.41 | 2.45 | 84 ± 11 |
| α-L FUDR | NT | 389,500 | NT |

NT = Not Tested

The results indicate that the prototype dimers inhibit the growth of murine-cultured leukemic L1210 and melanoma B16 cells with great potency (some $IC_{50}$ values of less than 1 nM.) The $IC_{50}$ values are several times more potent than FUdR. These results are unexpected and thus these compounds are truly unique.

The preliminary results of the telomerase inhibition are also intriguing. The α-L, β-D dimer inhibited the enzyme by 84% compared to control.

These data indicate that dimers containing an L-sugar have extremely interesting biological profiles and represent a novel class of potent antineoplastic agents. The activity profile of the L-dimers is different from that of the parent monomeric drug β-D-5FUdR.

The biological effects of the dimers were compared with those of the monomeric 5-FUdR on P388 leukemia and B16 melanoma cell lines. The results are shown in Table 2.

TABLE 2

In Vitro Testing Data

| CODE # | COMPOUND | IC50 (nM) P388 | B16 |
|---|---|---|---|
| L-102 | β-D-FUdR, α-L-FUdR | 0.71 | 3.0 |
| L-103 | α-L-FUdR, β-D-FUdR | 0.57 | 2.45 |
| L-107 | α-L-dU, β-D-FUdR | 7.0 | 219 |
| L-108 | α-L-FUdR, α-L-FUdR | 22,200 | 52,200 |
| L-109 | β-L-FUDR, β-L-FUdR | 5860 | 45,900 |
| L-110 | β-L-FUdR, β-D-FUdR | 2.0 | 6.3 |
| L-111 | α-L-dC, β-D-FUdR | 0.7 | 5.0 |
| — | β-D-FUdR | 2.8 | 28 |

These data indicate that the dinucleoside monophosphate compounds containing β-D-5FUdR in conjunction with α-L or P-L-nucleosides show superior in vitro activities against murine P388 leukemia and B16 melanoma cell lines, as is evidenced by lower $IC_{50}$ values. This indicates that such nucleoside dimers may indeed be acting by mechanisms different from those of 5-FUdR or are metabolized and/or transported differently from 5-FUdR.

EXAMPLE 6

Determination of Thymidylate Synthase Activity and its Inhibition in Intact L1210 Leukemia Cells In Vitro Thymidylate synthase is one suspected site of action of the compounds of the present invention against *P. falciparum*. Hence the skilled artisan would expect that the activity of selected compounds of the present invention, measured on thymidylate synthase activity measured in vitro, is a reliable indicium of the behavior of these compounds against *P. falciparum* infection in in vivo systems.

The mouse leukemia L1210 cells are harvested from the cell culture flasks and the cell concentration is determined. The cells are then resuspended in the desired amount of the medium to give a stock concentration $5 \times 10^7$ cells/mL. Series of the dilution of the stock solution of the compounds to be tested are prepared (concentrations are ranged from $10^8$ M to $10^{-3}$ M). The solution of the compound to be tested in the desired concentration is pipetted into a microcentrifuge tube and incubated at 37° C. using a shaking water bath. The reaction is started by addition of [5-$^3$H]-2'-deoxycytidine (10 μL, concentration of the stock solution—$10^{-5}$ M) after a 30 or 60 min. preincubation with 80 μL of the cell suspension and allowed to proceed for 30 min. in a shaking water bath at 37° C. The reaction is terminated by adding 100 μL of the 10% charcoal in 4% $HClO_4$. The tubes are vigorously stirred by vortexing and then centrifuged for 10 min. in a Beckman Microfuge. The radioactivity of a 100 μL of supernatant fraction from each tube is counted in a Packard Tri-Carb (model 2450 or 3255) liquid scintillation spectrometer using a toluene based scintillation mixture. The release of tritium is expressed as a percentage of the total amount of radioactivity added. $IC_{50}$ values determined from dose response curves represent the concentration of inhibitors required for 50% inhibition of the release of tritium. Table 3 below shows the results of the analysis of tritium release and determination of the $IC_{50}$.

TABLE 3

| Sample Code | Inhibition of Tritium Release, $IC_{50}$ (μM) |
|---|---|
| 5FUdR | 0.035 |
| L-102 | 0.035 |
| L-103 | 0.035 |
| L-107 | >100 |
| L-108 | >100 |
| L-109 | >100 |
| L-110 | 6 |
| L-111 | N/T |

EXAMPLE 7

In Vivo Testing of Dimers in P388 Leukemia B16 Melanoma

A. Experimental

1. P388 Leukemia

B6D2F1 mice received i.p. inocula of P388 murine leukemia cells prepared by removing ascites fluid containing P388 cells from tumored B6D2F1 mice, centrifuging the cells, and then resuspending the leukemia cells in saline. Mice received $1 \times 10^6$ P388 cells i.p. on day 0. On day 1, tumored mice were treated with the dimers or vehicle control. The route of drug administration was i.p. and the schedule selected was daily×5. The maximum tolerated doses (MTD) was 200 mg/kg for each dimer and was determined in initial dose experiments in non-tumored mice. In the actual experiments, L-103 was given at 100 mg/kg and 50 mg/kg.

2. B16 Melanoma

B6D2F1 mice received i.p. inocula of B16 murine melanoma brei prepared from B16 tumors growing s.c. in mice (day 0). On day 1, tumored mice were treated with the dimers or vehicle control. The route of drug administration was i.p. and the schedule selected was daily×5. The maximum tolerated doses (MTD) was 200 mg/kg for each dimer and was determined in initial dose experiments in non-tumored mice. In the actual experiments, L-103 was given at 100 mg/kg and 50 mg/kg.

3. Survival Standard

The mean survival times of all groups were calculated, and results are expressed as mean survival of treated mice/mean survival of control mice (T/C)×100%. A T/C value of 150 means that the mice in the treated group lived 50% longer than those of the control group; this is sometimes referred to as the increase in life span, or ILS value.

In the P388 studies, mice that survive for 30 days are considered long term survivors or cures while in B16; mice that survive for 60 days are considered long term survivors or cures. The universally accepted cut-off for activity in both models, which has been used for years by the NCI, is T/C=125. Conventional use of B16 and P388 over the years has set the following levels of activity: T/C<125, no activity; T/C=125–150, weak activity; T/C=150–200, modest activity; T/C=200–300, high activity; T/C>300, with long term survivors; excellent, curative activity.

B. Results

1. P388 Leukemia

L-103 demonstrated modest activity in the P388 leukemia in mice at all doses tested (Table 5). L-103 gave i.p. daily×5 at doses of 100 mg/kg and 50 mg/kg resulted in T/C values of 149 and 144 respectively. Fluorodeoxyuridine (FUdR) was used as the positive drug control in this study; FUdR produced a T/C=164 in the P388 test (Table 4). All agents were well-tolerated in this experiment; there was little or no body weight loss and no toxic deaths were recorded.

TABLE 4

L-103 vs. Murine P388 Leukemia

| Group | n | Dose | Weight Change (Day 7) | T/C |
|---|---|---|---|---|
| Control | (10) | 0.9% Saline | +9.1% | 100 |
| L-103 | (10) | 100 mg/kg | +1.5% | 149 |
| L-103 | (10) | 50 mg/kg | −1.6% | 144 |
| FUdR | (10) | 100 mg/kg | −2.7% | 164 |

2.B16 Melanoma

L-103 demonstrated modest activity against B16 melanoma implanted in mice (Table 5). L-103 (i.p.; daily×5) gave T/C values of 139 and 134 respectively. The positive control drug FUdR resulted in modest efficacy in the B16 test; a T/C value of 135 was obtained (Table 5). All agents were well-tolerated, with little or no weight loss; no drug-related deaths occurred.

TABLE 5

L-103 vs. Murine B16 Leukemia

| Group | n | Dose | Weight Change (Day 7) | T/C |
|---|---|---|---|---|
| Control | (10) | 0.9% Saline | +4.9% | 100 |
| L-103 | (10) | 100 mg/kg | +2.3% | 139 |
| L-103 | (10) | 50 mg/kg | +6.3% | 134 |
| FUdR | (10) | 100 mg/kg | −0.5% | 135 |

L-103 demonstrated modest activity against both the P388 and B16 experimental murine tumors at the two doses tested. L-103 was approximately as active as the positive control drug FUdR in the B16 test, and was somewhat less active than FUdR in the P388 test.

From the foregoing, the significance of L-sugar-based α- and β-enantiomeric nucleosides, nucleotides and their analogues as versatile, highly effective chemotherapeutic agents is apparent. Our results on derivatives of 5-FUdR show that L-5-FUdR-containing isomers are less toxic than those containing β-D-5FUdR, perhaps because they are not phosphorylated or transported as the latter. We have found that dimeric derivatives designed and prepared from a-L-5FUdR show very potent activity against P388 leukemia cells and B16 melanoma cell lines, exceeding that of β-D-5FUdR. They appear to have unusual mechanisms of action, including inhibition of telomerase.

EXAMPLE 8

In Vivo Activity of Nucleoside Analogs Against *P. falciparum*

A. In Vitro Culture of the Malarial Parasite

*P. falciparum*, FCQ27, was maintained in culture using the techniques described by Trager & Jensen (W. Traqer and J. B. Jensen, Science, 193 673–675 (1976)). Cultures containing 2% hematocrit suspensions of parasitized human type O+ erythrocytes in RPMI 1640 medium, supplemented with 25 mM HEPES-KOH, pH 7.2, 25 mM NaHCO$_3$ and 10% human type O+ serum (v/v) are maintained in modular incubator chambers at 37° C. in a gas mixture of 5% O$_2$, 5% CO$_2$ and 90% N$_2$. The isolate of *P. falciparum* used in these experiments was FCQ27, routinely maintained in synchronized or asynchronous in vitro cultures at low hematocrit.

B. In Vitro Toxicity Against *P. falciparum*

The potential toxicity of nucleoside analogues against *P. falciparum* in culture was tested in microtitre plates over the range of drug concentrations for 24 hours. The procedures for monitoring parasite viability is well established (A. M. Gero, H. V. Scott, W. J. O'Sullivan and R. I. Christopherson, Mol. Biochem. Parasitol. 34, 87–89 (1989)) and is based on radiolabelled hypoxanthine or isoleucine incorporation. The incorporation of [G-$^3$H]hypoxanthine into the nucleic acids of *P. falciparum* was used to assess the viability of the parasite in vitro. Microculture plates were prepared with each well containing 225 µl of a 2% hematocrit culture of asynchronous parasited erythrocytes (1% parasitized cells). Each plate, containing varying concentrations of the drug to be studied (up to 200 µM final concentration for initial screen), was incubated for 24 h at 37° C. in a gas mixture of 5% O$_2$, 5% CO$_2$ and 90% N$_2$, at which point [G-$^3$H] hypoxanthine was added to each well and the incubation continued under identical conditions for a further 18–20 h. The control infected cells (i.e. without drug), routinely reached a parasitemia of 6–8% before harvesting. Expediency was aided by 96-well plate counter using lactate dehydrogenase for the drug susceptibility assay (L. K. Basco, F. Marguet, M. T. Makler and J. Lebbras, Exp. Parasitol. 80, 260–271 (1995); M. T. Makler and D. J. Hinrichs; Am. J. Trop. Med. Hyg. 48, 205–210 (1993)). This assay gave the identical results to the hypoxanthine technique. In addition, for each experiment, microscopic counting of Giemsa stained thin slides was used as a control.

C. Transport and Metabolism in *P. falciparum* Infected Erythrocytes

The metabolism of the L-nucleoside conjugates was studied by HPLC analysis. The primary aim was to determine their ability to be catabolized by parasite purine salvage enzymes. Some effect on the purine metabolic pools was also observed.

For each HPLC determination 200 µL of packed cells of 80–90% trophozoite infected cells were used. These were isolated from in vitro cultures by synchronization of the parasites in in vitro cultures using sterile D-sorbitol (L. Lambros and J. P. Vanderberg, Parasitol. 65, 418–420 (1979)) followed by separation of the trophozoites from non infected erythrocytes by Percoll gradients as described previously (A. M. Gero, H. V. Scott, W. J. O'Sullivan and R. I. Christopherson, Mol. Biochem. Parasitol. 34, 87–89 (1989)). Trophozoites were incubated at 37° C. for 2 hours with each compound to be tested. Compounds were incubated with both whole infected cells as whole and lyzed uninfected normal erythrocytes to determine:

a) entry to the cell (whether they were transported);
b) the metabolic effect within the cell (was the compound metabolized);
c) the capacity of broken or lyzed cells to catabolize the compound which may not be able to enter the unbroken cell (i.e. if the compound was transported into the cell, would it be metabolized to the active form).

Drug incubation was terminated by centrifugation through silicon oil using the method of Upston and Gero (J. M. Upston and A. M. Gero, Biochem. Biophys. Acta. 1236, 249–258 (1995)). This procedure separated intact trophozoites from extracellular non-transported drug solution.

The metabolism of nucleosides with potential chemotherapeutic activity was assessed by the analysis of cytoplasmic samples by reverse phase ion-pair high performance liquid chromatography (R. S. Toguzov, Y. V. Tikhonov, A. M. Pimenov, V. Prokudin, Journal of Chromatography, I. Biomedical Appl. 434, 447–453 (1988)). Nucleotides, nucleosides and bases were separated by this HPLC method.

The transport and metabolism of purine nucleosides differ considerably between the normal human erythrocyte and human erythrocytes which have been infected with *Plasmodium falciparum*. The malaria parasite is unable to synthesize purines de novo and so therefore must rely on salvage pathways to obtain purines it requires for growth and division (L. W. Scheibel & T. W. Sherman, In: Malaria: Principles and practice of Malariology (W. H. Wernsdorfer & I. McGregor, Eds.) V. 1, 234–242 (1988)). Additionally, normal human erythrocytes do not contain significant levels of pyrimidine nucleotides (E. Szabodos & R. I. Christopherson, Biochem. Edu. 19, 90–94 (1991)), and the parasite is unable to obtain pyrimidine bases by salvage pathways and again has to rely on de novo synthesis (L. W. Scheibel & T. W. Sherman, In: Malaria: Principles and practice of Malariology (W. H. Wernsdorfer & I. McGregor, Eds.) V. 1, 234–242 (1988)). These modifications to the metabolic pathways of the infected erythrocytes, along with modifications of their transport system, represent significant variations from normal erythrocytes and may present an opportunity for the use of selectively toxic compounds against the parasites.

Nucleosides have attracted researchers as potential therapeutic agents. Naturally occurring nucleosides are usually in the β-D configuration. Therefore most of nucleoside analogues designed for the treatment of cancer, viral and parasitic diseases have been synthesized in this stereochemical configuration. Recent discoveries in our laboratories at the University of Georgia, the University of Iowa and at Yale University, as well as at universities in France and Italy, have confirmed that most L-nucleosides exhibit low toxicity because normal cells do not utilize them for building RNA or DNA and don't metabolize them. The discovery that 3TC (an approved treatment for HIV) was more potent and less toxic in its L-configuration than its enantiomer strongly supports the hypothesis that L-nucleosides and their conjugates could have therapeutic potential against invasive diseases such as cancer, viruses, and parasites (C. N. Chang, S. L. Doong et al. J. Biol. Chem. 267, 13939–13942 (1992); (H. Soudens, X. J. Yao, Q. Gao, B. Belleau, J. L. Kraus, N. Nguyen-Ba, B. Spira, M. A. Wainberg, Antimicrob. Agents Chemother. 35, 1386–1390 (1991); (T. S. Lin, M.-Z. Luo, M.-C. Liu, S. B. Pai, G. E. Dutschman & Y.-C. Chen, J. Med. Chem. 37, 798–803 (1994).

Recently, Dr. Gero and her coworkers discovered that the nonphysiological β-L-adenosine can be selectively transported into an erythrocyte infected with *P. falciparum* (A. M. Gero & J. M. Upston, In: Pyrine & Pyrimidine Metabolism in Man VIII (A. Sahota & M. Taylor, Eds) Plenum Press, NY, 495–498 (1995). Normal erythrocytes and other cell types are completely impermeable to this compound.

During the Phase I study, we used this unique ability of the non-natural nucleoside analogues for selective transport to the malaria infected cells to create a novel synthetic L-nucleoside based class of non-toxic antimalarial agents. Our working hypothesis was based on the design and biological evaluation of novel chemical entities which would consist of both 5-fluorodeoxyuridine (FUdR), a known inhibitor of thymidylate synthase, and an L-nucleoside or its derivatives. The number of "dimers" consisting of α- or β-L isomeric modification of physiological nucleosides or their derivatives was conjugated with FUdR by phosphate or pro-phosphate linkage. Along with anticancer activity, FUdR has a potential as an antimalarial agent (S. A. Queen, D. L. Vander Jagt & P. Reyer, Antimicrobial Agents & Chemotherapy. 34, 1393–1398 (1990). Unfortunately, FUdR's toxicity limits its use. In theory, combining FUdR with an L-nucleoside unit would result in an entity that could selectively transport an active component to infected cells while having no effect on normal cells.

During Phase I research a total of 42 L-nucleoside analogs were screened in an in vitro assay against *P. falciparum*. These compounds are shown in FIG. 7. From these forty-two compounds, 31 were available for screening from Lipitek International's library and 11 were specifically synthesized for the purpose of this project. The detailed synthesis of 11 L-nucleoside conjugates is described in the Methods and Procedures. They were prepared in 100 mg scale and were fully characterized by analytical methods (NMR, HPLC, mass spectra, TLC). The forty-two compounds tested were representative of L-nucleoside monomers or 4 different types of L-nucleosides conjugates. The conjugates tested were: a) dinucleoside phosphates, b) dinucleoside phosphorothioates, c) SATE derivatives of L-nucleosides, and d) L-nucleoside conjugates of nitrobenzylthioinosine (NBMPR). It should be emphasized that even more diversification resulted from utilizing characteristic to nucleosides 3' to 5' versus 5' to 3' phosphodiester linkages as well as variations of purines and pyrimidines in both parts of the dimers.

The biological screen involved evaluation of the compounds against the protozoan *P. falciparum* in in vitro culture. The range of drug concentrations was used independently by two assays. One, radiolabelled hypoxanthine incorporation into the nucleic acid of *P. falciparum*, and the other, more expedient assay, a 96-well plate susceptibility assay using lactate dehydrogenase. Both assays gave identical results. In addition, microscopic counting of Giemsa stained thin slides was used as a control. The results of the biological assays are presented in Table 1. Examples of experimental curves are attached as Appendix 2. The biological tests were done at several concentrations. The highest concentration was 200 AM, the compounds were considered active at concentrations less than 40 $\mu$M.

Discussions

In Vitro Activity

A careful analysis of the data presented in Table 6 (below) indicates that nine (9) analogs from 42 screened had $IC_{50}$ less than 40 $\mu$M (for the structure of the tested compounds see FIG. 7). The most active representative of dinucleoside phosphates were L-101, L-103, L-110, L-111, L-113, L-133 and L-138.

TABLE 6

Results of the in vitro testing

| N | CODE | COMPOUND | $IC_{50}$, $\mu$M |
|---|------|----------|-------------------|
| 1. | L-101 | [β-D]$_2$-FUdR | 15 |
| 2. | L-103 | [α-L,β-D]-FUdR | 20 |
| 3. | L-103 thio | [α-L,β-D]-FUdR, S = P – O | >200 |
| 4. | L-109 | [β-L]$_2$-FUdR | >200 |
| 5. | L-110 | [β-L, β-D]-FUdR | 20 |
| 6. | L-111 | α-L-dC, β-D-FUdR | 38 |
| 7. | L-113 | β-L-dC, β-D-FUdR | 17 |
| 8. | L-117 | β-L-dU, β-D-FUdR | 35 |
| 9. | L-117 thio | β-L-dU, β-D-FUdR S = P – O | >200 |
| 10. | L-125 | α-L-dA, β-D-FUdR | 60 |
| 11. | L-128 | [β-D, β-D-FUdR] S = P – O | 1.5 |
| 12. | L-133 | β-L-dG, β-D-FUdR | 14 |
| 13. | L-138 | β-L-dA, β-D-FUdR | 5 |
| 14. | L-138-thio | β-L-dA, β-D-FUdR, S = P – O | 100 |
| 15. | L-144 | β-D-FUdR, β-L-A | 140 |
| 16. | L-145 | β-L-dU, NBMPR | >200 |
| 17. | L-146 | α-L-dT, NBMPR | >200 |
| 18. | L-147 | NBMPR, MP | Solubility problem |
| 19. | NBMPR | NBMPR | 100 |
| 20. | GCI 1007 | α-L-erythrofuranosyl-5-fluorouracil | >200 |

TABLE 6-continued

Results of the in vitro testing

| N | CODE | COMPOUND | IC$_{50}$, μM |
|---|---|---|---|
| 21. | GCI 1018 | α-L-arabinofuranosyl adenine | >200 |
| 22. | GCI 1027 | α-L-FUdR | >200 |
| 23. | GCI 1030 | β-L-G | >200 |
| 24. | GCI 1032 | β-L-A | >200 |
| 25. | GCI 1033 | β-L-I | >200 |
| 26. | GCI 1034 | β-L-mercapto-G | >200 |
| 27. | GCI 1036 | β-L-Da | >200 |
| 28. | GCI 1037 | β-L-dI | >200 |
| 29. | GCI 1066 | α-L-A | >200 |
| 30. | GCI 1069 | α-L-dA | >200 |
| 31. | GCI 1070 | β-L-dG | >200 |
| 32. | GCI 1077 | β-L-ddA | >200 |
| 33. | GCI 1079 | α-L-ddA | >200 |
| 34. | GCI 1085 | N$^6$-methyl-β-L-A | >200 |
| 35. | GCI 1076 | 6-thio-β-L-purine | >200 |
| 36. | B01 | β-D-FUdR 3'SATE | 100 |
| 37. | B02 | β-D-FUdR 5'SATE | 60 |
| 38. | B03 | β-D-FUdR 3'–5'SATE | 6 |
| 39. | B04 | β-L-FUdR 5'SATE | 200 |
| 40. | B05 | β-L-FUdR 3'–5'SATE | Solubility problem |
| 41. | B06 | α-L-FUdR 5'SATE | 150 |
| 42. | B07 | α-L-FUdR 3'–5'SATE | Solubility problem |

The 14 L-nucleoside monomers in α- and β- forms and even α-L-FUdR showed no activity against *P. falciparum*. Because of that, further research on monomers was halted (see Table 6).

The dimer containing only the "non-natural" isomeric form of nucleoside (L-109) did not exhibit any activity.

Careful analysis of the data in Table 1 indicates that β-D-isomer of FUdR is the active component of the dimer molecules. The position of the active component in the dimer is important. The β-D-FUdR needs to be connected to the 3'-OH end of the L-nucleoside through a phosphodiester linkage to its 5'-OH. Compounds which are linked through 3'-OH of FUdR are much less active (see Table 7). This indicates that the substitution pattern of β-D-FUdR is critical for the activity of the dimers and most probably the mechanism involves thymidylate synthase inhibition. It is well known that TS inhibitors of FUdR have very rigid structural requirements and do not allow for any substitution at the 3' end.

TABLE 7

The activity of the L-nucleoside containing dimers versus position of FUdR linkage

| 5' | | 3' | |
|---|---|---|---|
| Compound | IC$_{50}$, μM | Compound | IC$_{50}$, μM |
| L-101 ([β-D]$_2$-FUdR) | 15 | L-144 (β-D-FUdR, β-L-A) | 140 |
| L-103 (α-L-FJdR, β-D-FUdR) | 20 | | |
| L-110 (β-L-FUdR, β-D-FUdR) | 20 | | |
| L-111 (α-L-dC, β-D-FUdR) | 38 | | |
| L-113 (β-L-dC, β-D-FUdR) | 17 | | |
| L-125 (α-L-dA, β-D-FUdR) | 60 | | |
| L-133 (β-L-dC, β-D-FUdR) | 14 | | |
| L-138 (β-L-dA, β-D-FUdR) | 5 | | |

In the case of purine nucleoside, the attachment of the α-L nucleoside to β-D-FUdR monomer reduces the dimer activity in comparison with dimers containing the β-unit (see Table 3, L-125 and L-138). In the case of pyrimidine nucleosides there is no obvious difference in the activity (L-103 & L-110, L-111 & L-113, Table 8).

TABLE 8

The activity of the dimers versus chemical configuration of the L-nucleoside

| α-L | | β-L | |
|---|---|---|---|
| Compound | IC$_{50}$, μM | Compound | IC$_{50}$, μM |
| L-103 (α-L-FUdR) | 20 | L-110 (β-L-FUdR) | 20 |
| L-111 (α-L-dC) | 38 | L-113 (β-L-dC) | 17 |
| L-125 (α-L-dA) | 60 | L-138 (β-L-dA) | 5 |

The different activity of the dimers is dependent on the structure of the second nucleoside.

The data presented above suggest that the following plausible pathways for metabolic activation and/or mode of action of the dimer molecules tested:

(1) Dimer may act as a new chemical entity without hydrolysis of the phosphate or pro-phosphate bond between the two monomeric units;

(2) Hydrolysis to L-nucleoside and FUdR nucleotide may occur, in which case the dimer is a prodrug. The L-nucleoside is used for protection and to increase the bioavailability of β-D-FUdR monophosphate.

It is also important to note that hydrolysis can take place intracellularly as well as outside the cell.

In the last decade, monumental efforts have been directed toward the synthesis of oligonucleotide analogs with altered phosphodiester linkage. The goal was to improve the stability of duplex and triplex formation, to improve the cellular uptake and to decrease the rate of degradation of oligonucleotides by endo and exo nucleases which cleave the phosphodiester linkage. We selected one such chemical modification for our study. As a consequence, several dimers with phosphorothioate linkage between two nucleosides were synthesized and tested. The phosphorothioate comprises a sulfur-for-oxygen substitution at phosphorus of the phosphodiester linkage (for the structure of the corresponding dimers see Appendix 1). It has been shown (M. Matsukura, K. Shinozuka, G. Zon, H. Mitsuya, M. Reitz, J. S. Cohen, L. M. Neckers, Proc. Natl. Acad. Sci. U.S.A. 84, 7706 (1987)) that the S homologues are more resistant to cellular nucleases and are readily taken up by cells. Several oligonucleotides of this type are currently in clinical studies (ISIS Pharmaceuticals and others).

TABLE 9

The activity of the dimers versus nature of the linkage between two nucleosides analogs

| Phosphate "bridge" O = P – O | IC$_{50}$, μM | Phosphorothioate "bridge" S = P – O | IC$_{50}$, μM |
|---|---|---|---|
| L-101 ([β-D]$_2$-FUdR) | 15 | L-128 ([β-D]$_2$-FUdR) | 1.5 |
| L-103 ([α-L,β-D]-FUdR) | 20 | L-103 ([α-L,β-D]-FUdR) | >200 |
| L-117 (β-L-dU, β-D-FUdR) | 35 | L-117 (β-L-dU, β-D-FUdR) | >200 |
| L-138 (β-L-da, β-D-FUdR) | 5 | L-138 (β-L-dA, β-D-FUdR) | 100 |

The replacement of the phosphate linkage by the phosphorothioate bond in the dimer, containing two β-D-FUdR units, increases the activity of the compounds by a factor of 10 (see Table 9, data for L-101 & L-128). The only active phosphorothioate analog appears to be compound L-128.

The activity of L-128 is greater in comparison with all possible products of hydrolysis (see Table 9). Moreover, L-128 was the most active compound tested.

TABLE 10

The activity of β-D-FUdR and some possible products of its metabolism

| COMPOUND | IC$_{50}$, μM |
|---|---|
| β-D-FUdR | 34 |
| β-D-5'-FUdRmP | 50 |
| 5FUracil | 6 |

The introduction of the phosphorothioate bond into molecules of dimers containing "non-natural" nucleoside isomer was not successful: the activity of the compounds was reduced dramatically (see Table 9, data for L-103, L-117 & L-138). As was discussed before, one of the possible mechanisms of dimer action is the participation in the metabolic pathways of the whole non-hydrolyzed molecule. In this case the increasing of the dimer stability by the introduction of the phosphorothioate linkage results in the increasing of the activity of L-101. For the dimers containing the "non-natural" isomeric modification of the nucleoside the metabolism of whole non-hydrolyzed molecule is probably impossible.

It is well established that most of the nucleoside analogs are dependent in kinase-mediated activation to generate the bioactive nucleotide and ultimately, the nucleoside triphosphate (C. Periqaud, G. Gosselin, J. L. Imbach, Nucleoside Nucleotides. 11, 903 (1992)). Activation takes place in the cytosol after nucleoside uptake and involves three successive viral and/or cellar kinases, the first one being highly specific (M. C. Starnes, Y. C. Cheng, J. Biol. Chem. 262, 988 (1987)). One possibility to improve the efficiency of the nucleoside analog is a therapeutic agent could be to bypass the phosphorylation step. Unfortunately, nucleoside monophosphates themselves, due to their polar nature, are not able to cross the cell membrane efficiently (K. C. Leibman, C. J. Heidelberg, J. Biol. Chem. 216, 823 (1995)). Hence the idea of temporarily masking or reducing the phosphate negative charges with neutral substituents, thereby forming more lipophilic derivatives which would be expected to revert back to the nucleoside mono-phosphate once inside the cell.

One of the possible structural modifications for the kinase bypass is the use of the bis-S-acetylthioethyl (SATE) derivatives pioneered by J.-L. Imbach (I. Lefebvre, C. Perigaud, A. Pompon, A. M. Auberth, J. L. Grardet, A. Kirn, G. Gosselin and J. L. Imbach, J. Med. Chem. 38, 3941–3950 (1995); C. Perigaud, G. Gosselin, I. Lefebvre, J. L. Girardet, S. Benzaria, I. Barber and J. L. Imbach, Bio. Org. Med. Chem. Lett. 3, 2521–2526 (1993)). Several SATE derivatives of FUdR isomers were synthesized and tested their in vitro activity against *P. falciparum*. The obtained results are listed in Table 11.

TABLE 11

The activity of the SATE derivatives of FUdR

| Compound | ID$_{50}$, μM |
|---|---|
| β-D-FUdR | 34 |
| β-D-FUdR monophosphate | 50 |
| B01 (β-D-FUdR 3' SATE) | 100 |
| B02 (β-D-FUdR 5' SATE) | 60 |
| B03 (β-D-FUdR 3',5' SATE) | 6 |

TABLE 11-continued

The activity of the SATE derivatives of FUdR

| Compound | ID$_{50}$, μM |
|---|---|
| β-L-FUdR | >200 |
| β-L-FUdR monophosphate | N/A |
| B04 (β-L-FUdR 5' SATE) | 200 |
| B05 (β-L-FUdR 3',5' SATE) | Solubility problem |
| α-L-FUdR | >200 |
| α-L-FUdR monophosphate | N/A |
| B06 (α-L-FUdR 5' SATE) | 150 |
| B07 (α-L-FUdR 3',5' SATE) | Solubility problem |

It should be emphasized that all of the SATE derivitization was performed on monomers of FUdR varying the conformation. Thus derivatives of α- and β D and L-FUdR were prepared. Three types of SATE analogs were produced, a) decorated at 5' of the nucleoside, b) decorated at 3' of the nucleoside, and c) decorated at both 3' and 5' of the nucleoside resulting in disubstitution.

Fifteen L-nucleoside dimers (L-101, L-103, L-103A, L-107, L-110, L-111, L-112, L-114, L-117, L-120, L-122, L-124, L-125, L-133 & L-138) from Lipitek's library were submitted for in vitro screen to the U.S. Army Antimalarial Test Program (for the structures of the compounds, see FIG. 7). The compounds have been tested for their activity against two *P. falciparum* strains: D6 (chloroquin non-resistant) and W2 (chloroquin resistant). Seven (7) of the tested compounds exhibited activities below 40 μM against both strains of *P. falciparum*. The most active dimers were L-101, L-110, L-112, L-117, L-133 & L-138.

The transport and Metabolism Study

It has been established that transport and uptake in parasite invaded cells is different from that of normal blood erythrocytes (A. M. Gero & A. M. Wood, In: Pyrine & Pyrimidine Methabolism in Man VII, Part A. (R. A. Harkness et al., Eds) Plenum Press, NY, 169–172 (1991)). Invasion by the malaria parasite comprises the cell membrane, allowing penetration of unnatural substances of various size and shape, whereas normal cells are very selective in uptake. It was shown that L-nucleosides and their derivatives easily penetrate invaded cells, while they have a very slow rate of uptake into normal cells, if they enter at all. In order to obtain preliminary data on transport, uptake and metabolism, the HPLC method was used to analyze the following 10 Lipitek compounds: L-101, L-103, L-109, L-111, L-117, L-133, L-138, GCI 1007, GCI 1027, GCI 1069.

HPLC retention times for standard compounds purchased from Sigma is presented in Table 12.

TABLE 12

HPLC Retention Time for the Standard Compounds

| Compound Nucleobase | R.t., min | Compound Nucleotide | R.t., min |
|---|---|---|---|
| Adenine | 4.93 | 5'AMP | 16.56 |
| Guanine | 5.38 | 3'AMP | 19.46 |
| Uracil | 4.37 | 5'ADP | 23.89 |
| Hypoxanthine | 5.59 | 5'-ATP | 30.09 |
| Nucleoside | | 5'GMP | 15.24 |
| Adenosine | 12.47 | 5'-GDP | 23.13 |
| Guanosine | 9.96 | 5'GTP | 29.01 |
| Inosine | 8.88 | 5'-UMP | 14.85 |
| Thymidine | 12.36 | FUdRMP | 16.40 |
| 2'-Deoxyadenosine | 12.29 | | |

TABLE 12-continued

HPLC Retention Time for the Standard Compounds

| Compound Nucleobase | R.t., min | Compound Nucleotide | R.t., min |
|---|---|---|---|
| 2'-Deoxyguanosine | 11.03 | | |
| 2'-Deoxyuridine | 7.41 | | |
| 2'-Deoxycytidine | 8.25 | | |
| FUdR | 10.21 | | |

These compounds were chosen for the identification of possible metabolites. In this experiment the compounds were incubated with both whole infected cells, and with whole and lysed uninfected cells, followed by the separation of unreacted compound and HPLC analysis.

The results are presented in Table 13:
Column 1 shows the retention times of the original compound (not incubated with any cells).
Column 2 shows the retention times of the original compound remaining after incubation with whole parasite infected cell.
Column 3 shows the metabolic products i.e. new peaks due to conversion of the original compound or alteration in the natural purine or pyrimidine profile of the infected cell.

TABLE 13

HPLC Retention Time of Lipitek's Compounds
Trophozoite Incubations

| Compound | Neat Injection | Unmetabolized Peak | Metabolic Product |
|---|---|---|---|
| L-138 | 18.17, 18.89 | 18.26 | 16.93, 15.73 |
| L-133 | 16.72 | 17.03 | 15.65 |
| L-101 | 19.05 | 19.01 | 10.62 |
| L-103 | 18.31 | 18.25 | — |
| L-117 | 17.41 | 17.61 | — |
| L-111 | 15.69 | 15.69 | — |
| L-109 | 16.36 | — | — |
| GCI 1027 | 10.21 | 10.61 | — |
| GCI 1007 | 12.61 | 12.42 | — |
| GCI 1069 | 12.29 | — | 9.65 |

All nucleosides monophosphate dimers containing β-D-FUdR unit in combination with any L-nucleosides (L-101, L-103, L-111, L-117, L-133, and L-138) as well as tested L-nucleoside monomer analogs (GCI 1007, GCI 1027 & GCI 1069) entered the infected cells. All these compounds were toxic against P. falciparum. The L-109, combination of two L-dimers, could not enter the infected cell, and was also not toxic.

Compounds L-101, L-133 & L-138 appear to be metabolized by the infected cells, each producing at least one new peak (see Table 13). It is possible that L-138 and L-133 may be cleaved to a nucleotide and nucleoside.

None of the above 10 compounds were found to enter normal erythrocyte. Metabolism of any of the above compounds did not occur in lysates of human erythrocytes or lymphocytes. So even if the compounds were able to get into the normal cells, the normal cells cannot metabolize them into active ingredients. This underscores again the low toxicity and the selectivity of the L-nucleoside conjugates disclosed and claimed in this Application.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

One skilled in the art readily appreciates that the patent invention is well adapted to carry out the objectives and obtain the ends and advantages mentioned as well as those inherent therein. Dimers, pharmaceutical compositions, treatments, methods, procedures and techniques described herein are presently representative of the preferred embodiments and are intended to be exemplary and are not intended as limitations of the scope. Changes therein and other uses will occur those skilled in the art which are encompassed within the spirit of the invention or defined by the scope of the pending claims.

What is claimed is:

1. A method for treating Plasmodium falciparum infection, a viral infection, or a parasitic infection in a mammal comprising administering to said mammal a compound having the formula:

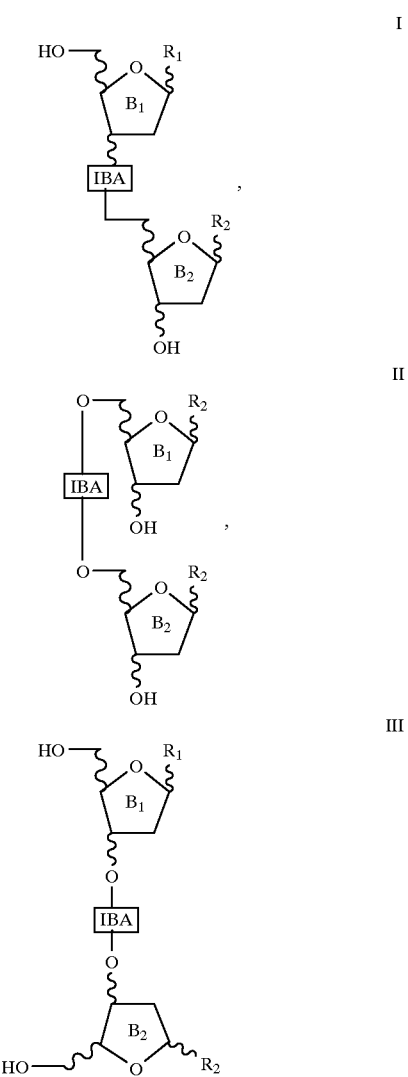

or a pharmaceutically acceptable salt thereof,
wherein:
$B_1$ and $B_2$ are each selected from the group consisting of β-D, β-L and α-L nucleosides and wherein at least one of $B_1$ or $B_2$ must be β-L or α-L nucleoside;
$R_1$ and $R_2$ are selected from the group of purine and pyrimidine bases consisting of cytosine, thymine, uracil, adenine, guanine, inosine, 5 fluorouridine (5 FUdR) and other 5-halopyrimidine bases; and wherein $R_1$ and $R_2$ are the same or a different base and wherein when $B_1$ or $B_2$ is attached to the internucleotide binding agent (IBA) at the 5' position and said $B_1$ or $B_2$ is β-L or α-L, then the $R_1$ or $R_2$ attached to said base cannot be cytosine; and IBA is selected from the linking groups consisting of phosphodiester, phosphorothioate, methoxy phosphotriesters, methylphosphonates, phosphorodithioates, phosphorothioates, silyl ethers, sulphonates and ethylenedioxy ethers.

2. The method of claim 1 wherein said compound is selected from the group consisting of 3'-O-(a-L-5-fluoro-2'-deoxyuridinyl)-β-D-5-fluoro-2'-deoxyuridine, (L-102), 3'-O-(β-D-5-fluoro-2'-deoxyuridinyl)-α-L-5-fluoro-2'-deoxyuridine, (L-103), 3'-O-(β-D-5-fluoro-2'-deoxyuridinyl)-α-L-2'-deoxyuridine, (L-107), 3'-O-(α-L-5-fluoro-2'-deoxyuridinyl)-α-L-5-fluoro-2'-deoxyuridine, (L-108), 3'-O-(β-L-5-fluoro-2'-deoxyuridinyl)-β-L-5-fluoro-2'-deoxyuridine, (L-109), 3'-O-(β-D-5-fluoro-2'-deoxyuridinyl)-β-L-5-fluoro-2'-deoxyuridine, (L-110), 3'-O-(β-D-5-fluoro-2'-deoxyuridinyl)-α-L-2'-deoxycytidine, (L-111), 3'-O-(β-D-5-fluoro-2'-deoxyuridinyl)-2'-deoxy-α-L-cytidine (L-113), 3'-O-(2'-deoxy-β-L-cytidinyl)-β-D-5-fluoro-2'-deoxyuridine (L-114), 3'-O-(2'-deoxy-α-L-cytidinyl)-β-D-5-fluoro-2'-deoxyuridine (L-115), 3'-O-(β-D-5-fluoro-2'-deoxyuridinyl)-β-L-2'-deoxyuridine (L-117), 3'-O-(β-L-5-fluoro-2'-deoxyuridinyl)-α-L-5-fluoro-2'-deoxyuridine (L-119), 3'-O-(β-5-fluoro-2'-deoxyuridinyl)-α-L-5-fluoro-2'-deoxyuridine (3', 3') (L-122) or a therapeutically acceptable salt thereof.

3. The method of claim 1 wherein the formula is I, $B_1$ is β-D, $B_2$ is α-L, $R_1$ and $R_2$ are both 5 FUdR, and IBA is a phosphodiester.

4. The method of claim 1 wherein the formula is II, $B_1$ is α-L, $B_2$ is β-D, $R_1$ and $R_2$ are both 5-FUdR, and IBA is a phosphodiester.

5. The method of claim 1 wherein the compound is 3'-O-(β-D-5-fluoro-2'-deoxyuridinyl)-α-L-5-fluoro-2'-deoxyuridine, (L-103).

6. The method of claim 1 wherein IBA is a phosphodiester linking group.

* * * * *